United States Patent [19]
Lerner et al.

[11] Patent Number: 5,601,992
[45] Date of Patent: Feb. 11, 1997

[54] PEPTIDE LIBRARY FORMATS AND METHODS RELATING THERETO

[75] Inventors: Michael R. Lerner; Channa K. Jayawickreme, both of Hamden, Conn.; Ethan A. Lerner, Brookline, Mass.

[73] Assignee: Bunsen Rush Laboratories, Inc., Newton, Mass.

[21] Appl. No.: 303,585

[22] Filed: Sep. 9, 1994

Related U.S. Application Data

[63] Continuation of Ser. No. 68,904, May 28, 1933, abandoned, which is a continuation-in-part of Ser. No. 917,502, Jul. 21, 1992, abandoned.

[51] Int. Cl.$^6$ .................................................. G01N 33/53
[52] U.S. Cl. ......................... 435/7.2; 435/7.1; 435/7.21; 435/7.23; 436/501
[58] Field of Search ............... 435/7.1, 7.2, 7.21, 435/7.23; 436/501, 518; 530/333, 354, 355

[56] References Cited

FOREIGN PATENT DOCUMENTS

| 9200091 | 1/1992 | WIPO . |
|---|---|---|
| WO92/01810 | 2/1992 | WIPO . |
| WO9309668 | 5/1993 | WIPO . |

OTHER PUBLICATIONS

Bray et al Tetrahedron Letters 23 #43 pp. 6163–6166 (21 Oct. 1991) "Gas Phase Clevage of Peptides from a Solid Support with Ammonia Vapour. Application in Simultaneous Multiple Peptide Synthesis".
Kohle et al Nature 256 pp. 495–497 (1975) "Continuous cultures at fused cells secreting antibody of predefined specifity".
Cremer et al in *Microbiological methods–5th ed.* edited by Collins pp. 167–181 (1984) "Antibiotic sensitivity and assay tests".
M. Lebl et al., Multiple release of equimolar amounts of peptides from a polymeric carrier using orthogonal linkage–cleavage chemistry, Intl J. of Peptide and Protein Research, vol. 41, No. 2, Feb. 2, 1993, pp. 201–203.
S. Birnbaum et al., Peptide Screening, Current Opinion in Biotechnology, vol. 3, No. 1, 1992, pp. 49–54.
A. Kassaejian et al., Screening of Synthetic Peptide Libraries with Radiolabled Acceptor Molecules, Peptide Research, vol. 6, No. 3, Jun. 1993, pp. 129–133.

A. S. Eison, et al., Science 215, 190 (1982), "Substance P Analog, DiMe–C7: Evidence for Stability in Rat Brain and Prolonged Central Actions".
R. T. Jensen, et al., Nature 309, 61 (1984), "A synthetic peptide that is a bombesin receptor antagonist".
G. Engberg, Nature 293, 222 (1981), "A synthetic peptide as an antagonist of substance P".
P. J. Woll, E. Rozengurt, Proc. Natl. Acad. Sci. 85, 1859 (1988), "[D–Arg, D–Phe, D–Trp Leu] substance P, a potent bombesin antagonist in murine Swiss 3T3 cells, inhibits the growth of human small cell lung cancer cells in vitro".
Lam, K. S. et al., "A New Type of Synthetic Peptide Library for Identifying Ligand–Binding Activity", Nature 354:82 (1991).
Fields, G. B., Tian, Z, Barany, G.; Principles and Practice of Solid–Phase Peptide Synthesis. In Synthetic Peptides: A User's Guide, G. a. Grant, ed., W. H. Freeman and Company, 1992, "Synthetic Peptides: Spanning the Twentieth Century".
Stewart, J. M., Young, J. D.; Solid Phase Peptide Synthesis, 2nd Ed., Pierce Chemical Co., Rockford, Illinois, 1984, "The Chemistry of Solid Phase Peptide Synthesis".
Atherton, E., Sheppard, R. C.; Solid Phase Peptide Synthesis: a practical approach, D. Rickwood and B. D. Hames, Eds. IRS Press, 1989, "Peptide Synthesis — An Introduction".
Fields, C. G., Lloyd, D. L., Macdonald, R. L. Ottenson, K. M., Noble, R. L.; HBTU activation for automated Fmoc solid phase peptide synthesis: Peptide Res. 4 (1991) 95–101.
Fields, G. B. and Noble, R. L.; Solid phase peptide synthesis utilizing 9–Fluorenylmethoxycarbonyl amino acids: 35 (1990) 161–214.

*Primary Examiner*—Lora M. Green
*Attorney, Agent, or Firm*—Wolf, Greenfield & Sacks, P.C.

[57] ABSTRACT

A method for detecting the interaction between an oligomeric molecule and a target is provided. A plurality of beads is applied to a substrate, each bead having associated therewith multiple copies of only a single oligomeric molecule. The beads are substantially spaced-apart from one another and are substantially immobilized on the substrate. Conditions are applied such that a substantial portion of the multiple copies associated with each bead can disassociate from and diffuse into the substrate, the substrate constructed and arranged to permit only substantially localized diffusion. A localized signal occurring as a result of the diffusion is detected. Coated beads and libraries of coated beads also are provided.

5 Claims, 6 Drawing Sheets

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

Trp  Ala  Val  Gly  His  Leu  Met
    1                            5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

```
    Met  Ile  Val  Gly  His  Leu  Leu
     1                 5
```

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

```
    Ser  Lys  Glu  Arg  His  Ser  Trp  Tyr
     1                 5
```

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Region
        ( B ) LOCATION: 1
        ( D ) OTHER INFORMATION: /label= Position_1
            / note= "Xaa at position 1 may be Ala, Arg, Asn,
            Asp, Gln, Glu, Gly, His, Ile, Leu, Lys, Met, Phe,
            Pro, Ser, Thr, Trp, Tyr or Val."

( i x ) FEATURE:
        ( A ) NAME/KEY: Region
        ( B ) LOCATION: 2
        ( D ) OTHER INFORMATION: /label= Position_2
            / note= "Xaa at position 2 may be Ala, Arg, Asn,
            Asp, Gln, Glu, Gly, His, Ile, Leu, Lys, Met, Phe,
            Pro, Ser, Thr, Trp, Tyr or Val."

( i x ) FEATURE:
        ( A ) NAME/KEY: Region
        ( B ) LOCATION: 7
        ( D ) OTHER INFORMATION: /label= Position_7
            / note= "Xaa at position 7 may be Leu, Met, Pro or
            Trp."

( x i ) SEQUENCE DESCRIPTION: SEQ ID NO:4:

```
    Xaa  Xaa  Val  Gly  His  Leu  Xaa
     1                 5
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

Trp Phe Val Gly His Leu Met
1               5

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:6:

Ala Trp Val Gly His Leu Met
1               5

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:7:

Phe Phe Val Gly His Leu Met
1               5

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:8:

Met Ile Val Gly His Leu Met
1               5

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:9:

His Tyr Val Gly His Leu Met
1               5

( 2 ) INFORMATION FOR SEQ ID NO:10:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

Phe Ala Val Gly His Leu Met
1               5

( 2 ) INFORMATION FOR SEQ ID NO:11:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:11:

Trp Ala Val Gly His Leu Met
1               5

PEPTIDE LIBRARY FORMATS AND METHODS RELATING THERETO

RELATED APPLICATIONS

This application is a continuation of Ser. No. 08/068,904, filed May 28, 1993 now abandoned, which is a continuation-in-part of U.S. application Ser. No. 07/917,502, filed Jul. 21, 1992 now abandoned, the entire disclosure of which is incorporated herein by reference.

FIELD OF THE INVENTION

This invention relates to peptide library formats and novel assays relating thereto.

BACKGROUND OF THE INVENTION

Peptides are the natural ligands for many receptors that regulate critical biological functions in humans. The traditional means of gaining insight into the manner in which peptides stimulate their receptors is to evaluate how amino acid substitutions within peptides affect their biological activities (A. S. Eison, et al., *Science* 215, 190 (1982); R. T. Jensen, et al., *Nature* 309, 61 (1984)).

Typically, small numbers of variants of a peptide ("congeners") are synthesized and the relative abilities of the congeners to activate the receptor are compared. Those variants having the greatest activation activity are selected for further evaluation. (see e.g., G. Enberg, *Nature* 293,222 (1981); P. J. Woll, E. Rozengurt, *Proc. Natl. Acad. Sci.* 85, 1859 (1988)).

Recently, the development of synthetic peptide combinatorial libraries ("SPCLs") on micro beads has made available large numbers of distinct peptides for studying ligand-receptor interactions. An SPCL can include anywhere from a few to many millions of different peptides. Typically, the peptides on any one bead in an SPCL library are the same; however, the peptide molecules can vary from bead to bead. See for example Lam, K. S. et al., "A New Type of Synthetic Peptide Library for Identifying Ligand-Binding Activity", *Nature* 354:82 (1991). Thus, if it is not necessary to remove the peptides from their supports to test them in a biological system, it is straight-forward to find a bead bearing a peptide of interest.

For many situations, however, the peptides must be dissociated from the bead so that the peptide is available to interact with a test system. For example, many peptides require that their carboxyl termini be free for them to be biologically active (M. L. Moore, in Synthetic Peptides: A User's Guide, G. A. Grant, ed. (W. H. Freeman and Company, New York, 1992)); however, many peptides are attached to the beads via their carboxyl termini, thus precluding biological activity of the bound peptide. As another example, while soluble antibodies can be brought to beads, many molecules of interest cannot (e.g. G-protein coupled receptors and other membrane bound proteins such as insulin receptors). As a third example, an antibiotic peptide that kills bacteria would be ineffective or substantially less effective in an assay if the peptide could reach only those bacteria immediately contacting a particular bead.

To address this problem, the above *Nature* paper suggests incorporating cleavable linkers during synthesis of each bead. The problem, however, is that if the peptides are released under standard conditions, i.e., in a solution, the peptides will mix together unless a single, or at most a few beads, are assayed at one time. This approach is not practical if evaluation of many peptides is desired.

SUMMARY OF THE INVENTION

A solution to the foregoing problems lies in releasing the peptides in an SPCL from their supports, but keeping the released peptides separate from each other, i.e., by creating mobile peptide libraries ("MPLs") from the SPCLs. This process advantageously offers the capability of freeing numerous peptides from a large number of beads while still keeping them individually localized. This is accomplished by separating the beads and releasing their associated peptides into a substrate which limits or prevents peptides of different sequences from mixing with one another.

Thus, according to one aspect of the invention, a method for detecting the interaction between an oligomeric molecule and a target is provided. A plurality of beads is applied to a substrate, each bead having associated therewith multiple copies of only a single oligomeric molecule, preferably in a manner such that the beads are substantially spaced-apart from one another and are substantially immobilized on the substrate. Conditions then are applied such that a substantial portion of the multiple copies associated with each bead disassociate from each bead and diffuse into the substrate, the substrate constructed and arranged to permit only substantially localized diffusion. A localized signal then is detected, the localized signal occurring as a result of the substantial portion diffusing and contacting a target. Preferably, the sequence of the oligomeric molecule that contacts the target is determined, e.g., by isolating at least one of the beads in the vicinity of the localized signal and sequencing the oligomeric molecule associated with the isolated bead.

The oligomeric molecules are covalently linked to the beads during construction of the library. In a preferred embodiment, at least some of the oligomeric molecules are released from the beads prior to performing the assays of the invention. However, the oligomeric molecules may alternatively be released from the beads subsequent to applying the beads to the substrate.

Surprisingly, it has been discovered that the covalent bonds between the oligomeric molecules and the beads may be cleaved under certain conditions wherein each oligomeric molecule remains associated with its respective bead. One way to accomplish this is to cleave the oligomeric molecules from the beads when the beads are in a "dry" state. For example, many beads can be placed in a container and can be exposed to a gas, e.g., air saturated with a cleaving agent, such as trifluoroacetic acid. After a few hours, a first portion of the oligomeric molecules is cleaved from, but continues to adhere to, the bead. By adjusting the cleavage conditions, e.g., increasing the time for the cleavage reaction or exposing the beads to a cleaving agent present in a liquid state, the selective release of a desired amount of the oligomeric molecules from the bead can be achieved. The cleaved oligomeric molecules can be removed from the bead, e.g., for amino acid sequencing, by placing the beads in a wash solution. Thus, the use of a linker having slow kinetics of cleavage with respect to the particular cleaving agent, permits the controlled release of partial amounts of the oligomeric molecules from the bead.

It also is possible to first apply the beads with their covalently attached oligomeric molecules to the substrate, and then apply conditions to cleave the bond between the oligomeric molecule and the bead. In either case, it is important to substantially immobilize the beads on the substrate so that oligomeric molecules released from the beads will diffuse only in a localized manner, thereby permitting one to associate a resultant signal with one or only a limited number of beads.

Thus, according to another aspect of the invention, a method for determining the relative potency of an oligomeric molecule for a target is provided. The method includes applying a plurality of beads having multiple copies of the oligomeric molecules associated therewith, to a substrate that is constructed and arranged to permit only localized diffusion of molecules. As discussed above, the oligomeric molecules can be covalently or non-covalently associated with the beads. If covalently attached to the beads, at least some of the covalent bonds are cleaved by exposing the bead to a cleaving agent either before, after or during application of the bead to the substrate. The oligomeric molecules are allowed to diffuse through the substrate to the target and the interaction of the oligomeric molecule with the target (as indicated by a localized signal) is measured at pre-selected time intervals. The relative potency of the oligomeric molecule for the target is proportional to the rate of change of the localized signal as a function of time.

According to a preferred aspect of the invention, not all of the oligomeric molecules are cleaved from covalent attachment to the beads. In particular, a substantial portion of the multiple copies associated with each bead are separated from covalent attachment to their respective beads while a substantial portion of the multiple copies remains covalently bound to their respective beads. This ensures that sufficient peptide remains associated with a bead whereby the peptide may be sequenced once the bead is isolated. One method to accomplish this is to attach the oligomeric molecules to the beads using two or more linkers, such that the oligomeric molecules are coupled through different linkages and are selectively and separately releasable via distinct or different means. In this manner, the amount of oligomeric molecule released for the biological assay and the amount of oligomeric molecule retained on the bead for subsequent sequencing can be controlled.

Alternatively, and in accordance with a more preferred aspect of the invention, the oligomeric molecules are attached to the beads by a first linker to form a coated support, the first linker clearable at a first bond by a first cleaving agent. The coated support is contacted with the first cleaving agent under conditions whereby a sufficient number of the first bonds are cleaved to release only a first substantial portion of the oligomeric molecules from the support. A second substantial portion remains attached to the beads. The conditions can include using a cleaving agent that is relatively slow acting upon the linker, whereby only a portion of the bonds are cleaved when the cleaving agent is applied for a given period of time.

Typically, the oligomeric molecule further includes a protecting group attached to the oligomeric molecule at a second bond. Preferably, the second bond is cleaved and the protecting group is removed prior to releasing the first substantial portion of the oligomeric molecules from the support. In the most preferred embodiments, the first bond has a free energy of activation for cleavage that is substantially greater than the free energy of activation for cleavage of the second bond. Accordingly, stronger cleaving conditions are required to release the oligomeric molecule from the support than are required to deprotect the molecule. For example, by sequentially applying cleaving agents of increasing strength (or a particular cleaving agent in a dilute and concentrated form), the oligomeric molecule can be completely deprotected prior to its release from the support.

Because the first bond has a relatively high activation energy for a cleavage reaction, the linker cleavage conditions can be selected to achieve the sequential release of oligomeric molecules from the solid support. Thus, the coated support can be contacted with a cleaving agent that will cleave only a portion of the bonds in a given period of time, and a partial release of oligomeric molecules from the support can be achieved.

In the preferred embodiments, a first set of cleavage conditions is selected to cleave only a first substantial portion of the oligomeric molecules, and then a second set of cleavage conditions (which may be identical to the first set) is selected to cleave a second substantial portion of oligomeric molecules from the support. Preferably, the first set of cleavage conditions releases the first substantial portion of the oligomeric molecules from their respective beads of origin while maintaining the molecules' association with the bead. In this manner, the controlled release of oligomeric molecules from the bead, as well as the identification of the oligomeric molecules with a particular source of beads, can be achieved.

According to another aspect of the invention, novel beads and libraries are provided. In the preferred embodiments, the invention utilizes a bead coated with multiple copies of only a single oligomeric molecule, substantially all of the oligomeric molecules being non-covalently bound to the bead. Preferably, the oligomeric molecule is a peptide, an oligonucleotide or a glycan (e.g., a glycosaminoglycan-type cell-surface carbohydrate). A library of such beads also is provided.

According to another aspect of the invention, there is provided a bead coated with multiple copies of only a single oligomeric molecule. A first substantial portion of the multiple copies is attached to the bead by a first covalent bond cleavable by a first agent, and a second substantial portion of the multiple copies is attached to the bead only by covalent bonds that are non-cleavable by the first agent, whereby the first substantial portion can be selectively released from covalent attachment to the bead relative to the second substantial portion. The second substantial portion is attached to the bead by a second covalent bond that is cleavable by a second agent, with the first substantial portion being attached to the bead only by covalent bonds that are non-cleavable by the second agent. Thus, the first substantial portion can be covalently attached to the bead by a first linker and the second substantial portion is covalently attached to the bead by a second linker.

In the preferred embodiments, the first and second substantial portions can be covalently attached to the bead via the same linker. According to this embodiment, each linker includes an internal bond and each oligomeric molecule is attached to a protecting group by a protecting group bond. The internal bond and the protecting group bond are subject to differential cleavage by one or more sets of conditions. Preferably, the internal bond has a higher activation energy than the protecting group bond.

BRIEF DESCRIPTION OF THE DRAWINGS

FIG. 1-a shows HPLC fractions of 500 pmol of litorin standard; FIG. 1-b shows HPLC fraction of synthetic litorin cleaved from 225 beads by exposure to gaseous TFA for 6 hours;

FIG. 1-c shows the kinetics of bond cleavage as determined by measuring the amount of litorin released from the beads upon exposure to gaseous TFA;

FIG. 3A shows a video image analysis resulting from 30 minutes exposure to the MPL. FIGS. 3B and 3C show the responses of recombinant melanophore cells to peptide from beads 6 (sequence ID No. 4, FAVGHLM) and 7 (sequence ID No. 1, WAVGHLM) at 25, 35 and 45 minutes, respectively;

FIGS. 7A–7C illustrate HPLC analysis of a-MSH released from polystyrene beads by treatment with TFA vapor; The fractionation of 60 pmols of an a-MSH—standard by analytical HPLC is depicted in FIG. 7a. FIG. 7b shows that synthetic hormone cleaved from the beads, by exposure to TFA gas, migrates identically to the control. FIG. 7c illustrates that the dry release method frees essentially all peptide from their beads as there is little detectable a-MSH remaining if the gas phase treated resin is washed, and then reexposed to TFA for a second time but in solution; FIG. 8b shows the placement of two a-MSH-bearing and two control peptide-bearing, TFA-treated beads on the surface of the gel after two minutes. As peptides continued to diffuse outward from the four source beads, the circles of responding pigment cells surrounding the two a-MSH bearing beads enlarged are shown in FIG. 8c, 30 minutes after placement of the beads.

DETAILED DESCRIPTION OF THE PREFERRED EMBODIMENT

Figure 1A:
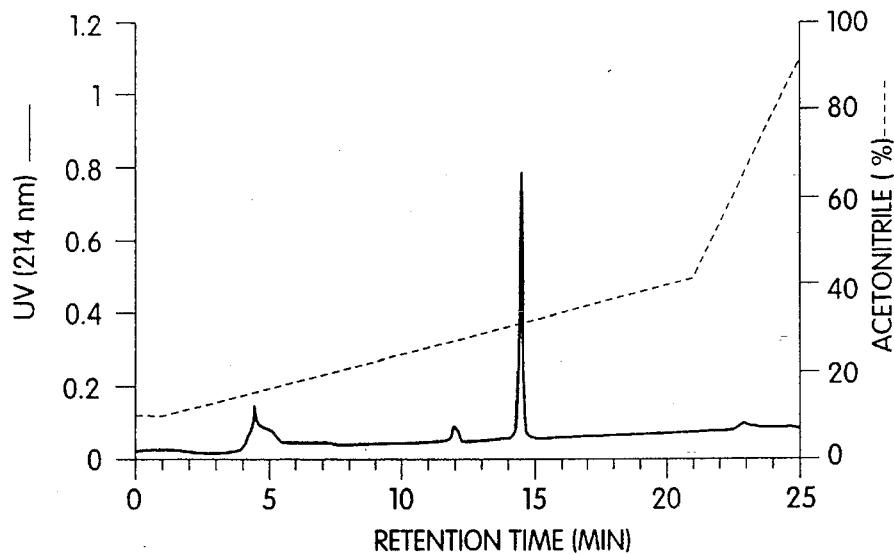
FIGS. 1A–1C illustrate the HPLC analysis of litorin released from polystyrene beads by a gas phase cleavage procedure.

The invention involves the use of libraries of oligomeric molecules attached to solid supports. In many of the preferred embodiments, the molecules on any particular bead are the same. According to one aspect of the invention, beads or assay protocols are provided whereby the molecules remain localized when the covalent bond between the molecule and the bead is cleaved and whereby the molecules, once released from association with a particular bead, do not mix with the molecules released from other beads.

The preferred solid supports are microparticle beads; however, the term "support" embraces any support to which a linker can be attached, e.g., microparticle beads, membranes, sephadex and silica particles, as well as magnetic particles. The preferred solid supports are microparticle beads upon which the oligomeric molecules of interest can be constructed and covalently attached. Preferred beads are formed of polystyrene. The most preferred beads are formed of 1% divinylbenzene (DVB) crosslinked polystyrene, which beads retain the peptides even after the covalent bonds are cleaved. As described in the Examples, beads having covalently attached linkers, as well as beads having a first amino acid covalently attached thereto via a first linker, are commercially available.

The size of the beads may vary widely, although it should be large enough to support a sufficient amount of oligomeric molecules to achieve the purposes of the invention. Bead sizes of about 100–200 mesh work well as they easily support a sufficient amount of oligomeric molecules and, at the same time, are capable of physical manipulation. In the preferred embodiments, each bead has between about 100 and 300 picomoles of oligomeric molecule attached thereto. It is believed that between about 1 to about 10 picomoles is sufficient for sequencing a peptide and that even less is necessary to produce a detectable signal in the assays of the invention.

The invention is particularly useful when attempting to screen large libraries of oligomeric molecules that can be constructed on beads. As used herein, the term oligomeric molecule embraces peptides, oligonucleotides, and glycans, as well as other similar entities that can be constructed in wide variety on a solid support. Analogues of the foregoing also are contemplated as will be readily understood by those of ordinary skill in the art. Exemplary peptide analogues ("congeners") of litorin, a peptide which binds to the bombesin receptor, are provided in the Examples.

Libraries of peptides can be screened, for example, for their ability to bind to proteins (e.g., receptors) or for their ability to bind to oligonucleotides. Similarly, oligonucleotide libraries of the instant invention can be screened for their ability to bind to other molecules. Thus, as used herein, a library means at least a few, and preferably, tens of thousands of molecular entities with different sequences. Accordingly, a library can include virtually millions of peptides or oligonucleotides having different sequences.

The oligomeric molecules are attached to the beads by linkers. A linker is a molecule that provides a covalent bridge between the bead and the oligomeric molecule. The oligomeric molecule is released from the support by exposing the coated support to one or more cleaving agents which cleave either: (1) the bond between the linking agent and the oligomeric molecule, thereby releasing the 'native' oligomeric molecule from the support, or (2) an internal bond of the linker.

In the preferred embodiments, the term "first cleavage agent" refers to agents capable of cleaving a selected bond within the linker, referred to herein as a "linker internal bond" or "first bond", thereby releasing the oligomeric molecules from covalent association with the bead. Exemplary linkers including such cleavable internal bonds are listed in Table 1. Exemplary cleavage agents capable of cleaving the internal bonds of these linkers are described below. For the linkers listed in Table 1, the released peptides typically include a terminal carboxyl group or a terminal amide group, depending upon whether the linker contributed a hydroxyl- or amino- group, respectively, following cleavage of the linker internal bond.

In the most preferred embodiments, the oligomeric molecules are attached to the bead with a first linker and various cleavage conditions are applied to the bead to release different portions of the plurality of oligomeric molecules from the bead. Thus, a first substantial portion of the plurality of molecules is released by exposing the beads to a first set of conditions and a second substantial portion of the plurality of molecules is released by exposing the beads to a second set of conditions. The first set of conditions can include, for example, contacting the beads with a cleavage agent for a selected period of time, followed by contacting the beads with a second set of cleavage conditions. The second set of cleavage conditions can be the same or different from the first set of conditions. Thus, the second set of conditions can include merely reexposing the bead to the first set of conditions. Alternatively, the first set of conditions can include contacting the beads with a first cleavage agent for a first period of time and the second set of conditions can include contacting the beads with the same cleavage agent for a second period of time. In this manner, the cleavage conditions can be varied to achieve the controlled release of pre-selected amounts of oligomeric molecules from the bead. Thus, selection of a linker having an internal first bond cleavable at a slow kinetic rate by a first cleaving agent permits the controlled release of the oligomeric molecules from the bead, e.g., by adjusting the length of time that the beads are exposed to the cleavage agent or the concentration of the cleavage agent. In principle, an entire SPCL (formed with a single linker) can be converted into an MPL (mobile peptide library) in a sequential manner by subjecting the SPCL to repeated rounds of cleavage conditions using the same cleavage agent (see the Examples).

For those embodiments in which the oligomeric molecule includes reactive groups that are coupled to protecting groups (described below), the preferred linker is further characterized in including a first bond having a substantially greater energy of activation for cleavage relative to the energy of activation for cleavage of the protecting groups. Thus, the instant invention also provides a method for the preferential deprotection of oligomeric molecule-coated supports without releasing the oligomeric molecule from the support.

Exemplary preferred linkers and cleavage agents for the controlled release of oligomeric molecules from a solid support are shown in Table 1. Additional useful linkers and cleaving agents are set forth in Table 2.

TABLE 1

Resin Linkers and Handles[3]

| Linker/Handle/Resin | | Cleavage Conditions | Resulting C-Terminus | References(s) |
|---|---|---|---|---|
| 4-Chloromethyl resin | | Strong acid | Acid | Gurre and Merrifield, 1971 Stewart and Young, 1984 |
|  | (1) | | | |
| 4-Hydroxymethylphenylacetic acid (PAM) | | Strong acid | Acid | Mitchell et al., 1978 Tam et al., 1979 |
| 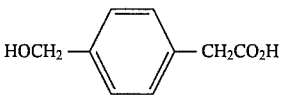 | (2) | | | |
| 4-Methylbenzhydrylamine resin (MBHA) | | Strong acid | Amide | Matsueda and Stewart, 1981 Gachde and Matsueda, 1981 |
| 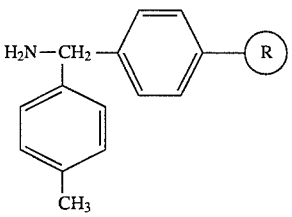 | (3) | | | |
| 3-Nitro-4-(2-hydroxyethyl)benzoic acid (NPE) | | Piperidine DBU | Acid | Eritja et al., 1991 Albericio et al., 1991b |
| 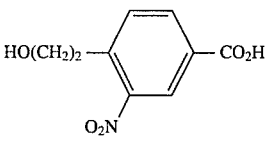 | (4) | | | |
| 9-(Hydroxymethyl)-2-fluoreneacetic acid (HMFA) | | Piperidine | Acid | Mutter and Bellof, 1984[c] Liu et al., 1990 |
| 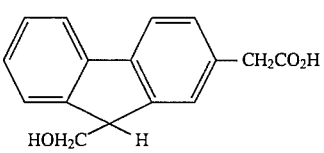 | (5) | | | |
| α- Bromophenacyl | | hv (350 nm) | Acid | Wang, 1976 |

TABLE 1-continued

Resin Linkers and Handles[3]

| Linker/Handle/Resin | | Cleavage Conditions | Resulting C-Terminus | References(s) |
|---|---|---|---|---|
| Br—CH(CH₃)—C(=O)—C₆H₄—CH₂CO₂H | (6) | | | |
| 3-Nitro-4-hydroxymethylbenzoic acid (ONb) | | hv (350 nm) | Acid | Rich and Gurwara, 1975[c]<br>Giralt et al., 1982<br>Barany and Albericio, 1985<br>Kneib-Cordonier et al., 1990 |
| HOCH₂—C₆H₃(O₂N)—CO₂H | (7) | | | |
| 3-Nitro-4-aminomethylbenzoic acid (Nonb) | | hv (350 nm) | Amide | Hammer et al., 1990 |
| H₂N(CH₂)₂—C₆H₃(O₂N)—CO₂H | (8) | | | |
| 4-Nitrobenzophenone oxime resin | | HOPip<br>AA→⁺N(nBu)₄<br>AA—NH₂ | Acid[b]<br>Amide | DeGrado and Kaiser, 1982[c]<br>Findeis and Kaiser, 1989<br>Scarr and Findeis, 1990 |
| HO—N=C(C₆H₄—R)(C₆H₄—NO₂) | (9) | | | |
| Hydroxy-crotonyl-aminomethyl resin (HYCRAM ™) | | Pd(0) +<br>NMM or<br>dimedone | Acid | Kunz and Dombo, 1988<br>Guibe et al., 1989<br>Lloyd-Williams et al., 1991b |
| HO—CH=CH—C(=O)—NH—CH₂—C₆H₄—R | (10) | | | |

TABLE 2

| STRUCTURE | Cleavage Agent | Resulting Carboxy Terminus |
|---|---|---|
| HOCH₂—C₆H₄—OCH₂—C₆H₄—P<br>(1) 4-alkoxybenzyl alcohol resin | TFA | Free Acid |
| HOCH₂—C₆H₄—OCH₂CO₂H<br>(2) (4-hydroxymethylphenoxyacetic acid | TFA | Free Acid |

TABLE 2-continued

| STRUCTURE | Cleavage Agent | Resulting Carboxy Terminus |
|---|---|---|
| 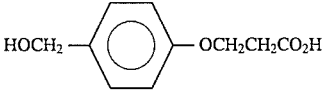<br>(3) 3-(4-hydroxymethylphenoxy)propionic acid | TFA | Free Acid |
| <br>(4) 4-hydroxymethylphenylacetic acid | TFMSA | Free Acid |
| 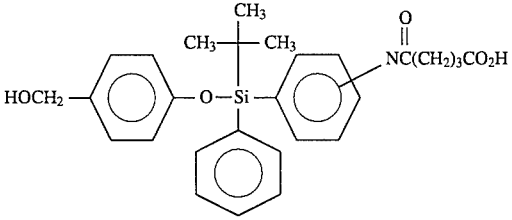<br>(5) (3 or 4)-((((4-hydroxymethyl)phenoxy-t-butyl-phenyl)-silyl)phenyl) pentanedioic acid monoamide | TBAF | Free Acid |
| 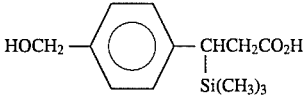<br>(6) 3-(4-hydroxymethylphenyl)-3-trimethylsilylpropionic acid | TBAF | Free Acid |
| 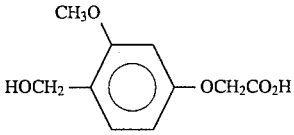<br>(7) 2-methoxy-4-hydroxymethylphenoxyacetic acid | Dilute TFA | Free Acid |
| 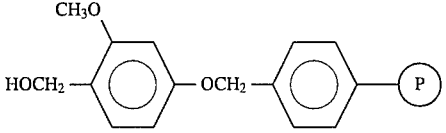<br>(8) 2-methoxy-4-alkoxybenzyl alcohol resin | Dilute TFA | Free Acid |
| 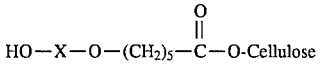<br>(9) allyl handle, X = $-CH_2-CH=CH-CH_2-$ or $-CH_2-C_6H_4-$ | Pd(0) | Free Acid |
| 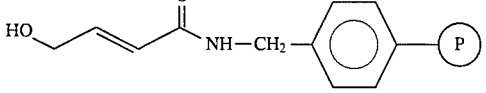<br>(10) hydroxy-crotonyl-aminomethyl resin | Pd(0) | Free acid |

TABLE 2-continued

| STRUCTURE | Cleavage Agent | Resulting Carboxy Terminus |
|---|---|---|
| (11) 2-chlorotrityl chloride resin | AcOH | Free acid |
| (12) 3-nitro-4-hydroxymethylbenzoic acid | hv(350 nm) | Free acid |
| (13) p-nitrobenzhydrylamine resin | H$_2$/Pd | Amide |
| (14) 4-(2',4'-dimethoxyphenylaminomethyl)-phenoxymethyl resin | Dilute TFA, AcOH | Amide |
| (15) 2,4-dimethoxybenzhydrylamine resin | TFA | Amide |
| (16) 4-(4'-methoxybenzhydryl)-phenoxyacetic acid | TFA | Amide |
| (17) 9-xanthenyl resin | Dilute TFA | Amide |

TABLE 2-continued

| STRUCTURE | Cleavage Agent | Resulting Carboxy Terminus |
|---|---|---|
| (18) 5-(4-aminomethyl-3,5-dimethoxyphenoxy)-valeric acid — structure shows a benzene ring with CH$_3$O groups at two positions, H$_2$NCH$_2$– substituent, and –O(CH$_2$)$_4$CO$_2$H substituent | TFA | Amide |
| (19) 3-(amino-4-methoxybenzyl)-4-methoxyphenylpropionic acid — structure with CH$_3$O–phenyl–CH(NH$_2$)–phenyl(CH$_3$O)–R, CH$_2$CH$_2$CO$_2$H; R = OCH$_3$, R = H | Dilute TFA<br>Me$_3$SiBr/TFA | Amide<br>Amide |
| (20) 4-succinylamino-2,2',4'-trimethoxybenzhydrylamine resin — structure with CH$_3$O–phenyl–CH($^+$NH$_2$Cl)–phenyl(CH$_3$O, OCH$_3$)–NHC(CH$_2$)$_2$CNHCH$_2$–P | TFA | Amide |
| (21) 4-(p-nitrophenoxycarbonyl-oxymethyl)phenoxy acetic phenacyl ester — NO$_2$–phenyl–OCOCH$_2$–phenyl–OCH$_2$COCH$_2$C–phenyl | TFA | Amide |
| (22) 3-(p-benzyloxyphenyl)-1,1-dimethyl-propyloxycarbonyl-hydrazide resin — H$_2$NNHCO$_2$C(CH$_3$)$_2$CH$_2$CH$_2$–phenyl–OCH$_2$–phenyl–P | TFA | Hydrazide |
| (23) 2-[4-(hydroxymethyl)phenoxy]-propionyl resin — HOCH$_2$–phenyl–OCHC(CH$_3$)(=O)–phenyl–P; A↑ at HOCH$_2$, B↑ at OCH | A: TFA<br>B: hv(350 nm) | Free Acid<br>4-hydroxy-benzyl ester |
| Structure with O$_2$N substituent: HOCH$_2$–phenyl–OCH$_2$–phenyl(O$_2$N)–C(=O)–NHCH$_2$–phenyl–P; A↑ at HOCH$_2$, B↑ at OCH$_2$ | A: TFA<br>B: hv(350 nm) | Free Acid<br>4-hydroxy-benzyl ester |

The linkers of Table 1 have in common an internal first bond characterized by slow kinetics of cleavage with respect to a first cleaving agent. In general, the controlled release of oligomeric molecules from a support in which the oligomeric molecules are attached via these linkers, is achieved by contacting the coated support with a first cleaving agent under conditions to cleave a sufficient number of the linker internal first bonds, thereby releasing a first substantial portion of the oligomeric molecules from the support. By "substantial portion" is meant a sufficient number of molecules to achieve the purposes of the invention. Thus, for example, if the purpose of the invention is to sequence a peptide attached to the support, then a substantial portion of peptide is that amount of peptide necessary for sequence analysis.

A description of the formation of a peptide-coated support, in which a peptide is attached to the support via a first linker, follows. Briefly, the peptide is assembled on the support by initially coupling a first amino acid (the carboxy terminal amino acid of the peptide) to the linker and sequentially coupling additional amino acids to the first amino acid until a peptide having the desired composition is completed. The following example is illustrative only and is not intended to limit the scope of the instant invention in any way.

In general, each amino acid to be incorporated into the peptide-coated support must be reacted with a "protecting agent" prior to attachment to the support and/or prior to attachment to a first amino acid previously coupled to the support. As used herein, protecting agent refers to a molecule that can be covalently attached to a reactive group of the oligomeric molecule for the purpose of protecting the reactive group from participating in undesirable side reactions. For an oligomeric molecule that is a peptide, such potentially reactive groups include the N-terminal amine group and reactive amino acid side chain groups. Typically, tBoc (tert- butyloxycarbonyl) and/or Fmoc (9-fluorenylmethyloxycarbonyl) chemistry is used to protect the amino acid reactive groups.

Various protecting agents are available for attachment to amino acid side chain reactive groups. Typically, these protecting agents are divided into three categories, depending upon whether the protecting agent is compatible with: (1) tBoc chemistry; (2) Fmoc chemistry; or (3) both tBoc and Fmoc chemistries. Exemplary side chain protecting agents for each of the above-identified categories are described in Scientific Peptides: A User's Guide,eds. G. Grant, W. H. Freeman & Co., New York, USA (1992).

To attach a first "protected" amino acid (i.e., an amino acid including one or more protecting agents) to the linker, the linker-coated support (commercially available from a variety of sources, including 4-methylbenzhydrylamine resin, Nova Blochem., California, USA) is contacted with the protected amino acid under conditions for forming a covalent bond between the linker and the amino acid. Next, the protecting group is removed from the N-terminal amine of the amino acid. Typically, N-terminal amines protected by Fmoc or tBoc, are "deprotected" (i.e., the protecting agent is cleaved therefrom) by contacting the (N-terminal protected) amino acid-coated support with piperidine or TFA (trifluoracetic acid), respectively. Protecting groups attached to reactive side groups optionally are then cleaved in accordance with methods described herein.

To attach a second amino acid to the first amino acid-coated support, the second amino acid is protected (as described above) and is contacted with the (deprotected) first amino acid-coated support under conditions to form a peptide bond between the free N-terminal amine of the immobilized first amino acid and the carboxyl terminal of the second (protected) amino acid. Deprotection of the second amino acid is then performed as described above. As would be apparent to one of ordinary skill in the art, deprotection of the N-terminal amine for each successive amino acid must be performed prior to covalently attaching the next amino acid to the growing peptide chain. As will also be apparent to one of ordinary skill in the art, deprotection of the side chain reactive groups may be performed at any time, including e.g., after each amino acid is covalently attached to the growing chain, or after the last amino acid has been attached. This process of sequentially reacting the coated support with a protected amino acid, followed by deprotecting (at least) the N-terminal amine of the newly added amino acid, is repeated until a peptide having the desired composition is attached to the support.

In the preferred embodiments, a substantial portion of the complete peptide is released from the support by contacting the peptide-coated support with a first cleaving agent under conditions to cleave a sufficient number of linker internal bonds (i.e., first bonds). By sufficient number is meant that number of first bonds, the cleavage of which will result in the release of a substantial portion of peptide. A "substantial portion" of oligomeric molecules (e.g., peptides) has previously been defined to mean that number of molecules necessary to achieve the purposes of the invention.

In general, the preferred linkers (see, e.g., Table 1) include a terminal hydroxyl or amine group that is capable of reacting with the carboxyl terminal end of the first protected amino acid to form a first amino acid-coated support. A preferred linker further includes a first bond that has a relatively high energy of activation for cleavage, i.e., the first bond exhibits slow cleavage kinetics by a first cleaving agent. In contrast to a less preferred linker having an internal bond that is capable of relatively rapid cleavage kinetics (see, e.g., Table 2, compound nos. 7 and 8), a preferred linker does not include electron withdrawing groups (e.g., methoxy groups, NO2 groups) for rendering the first bond more susceptible to nucleophilic attack by the first cleaving agent. As will be apparent to one of ordinary skill in the art, a slow rate of cleavage is desirable to achieve the controlled release of partial amounts of oligomeric molecules from the support. Thus, for example, if substantially all of the linker first bond can be rapidly cleaved by a strong acid, the controlled release of some, but not all, peptides from the support can be achieved by contacting the peptide coated-support with a dilute solution of the strong acid and/or by limiting the period of time that the coated support is exposed to the acid.

Typically, the peptide attached to the support includes at least one protecting group that is covalently attached to the peptide at a second bond (e.g., at the N-terminal amine). The instant invention thus provides a method for the sequential deprotection and controlled release of the deprotected peptide from the support by setting forth the following interdependent criteria for linker and protecting group selection: (1) the linker must include a first bond that is capable of being cleaved at a slow kinetic rate (for the controlled release of deprotected peptide from the support); and (2) the covalent bond ("second bond") formed between the protecting group and the peptide must be more susceptible to cleavage than the first bond, i.e., the second bond must have a lower activation of energy for cleavage relative to the activation of energy for cleavage of the first bond. Thus, "interdependent selection" refers to the process for choosing a combination of linker and protective group coupling chemistries such that the protective group is preferentially cleaved from the coated support, thereby permitting the controlled release of peptide in a deprotected form from the support.

Accordingly, in the most preferred embodiments, the first bond has an energy of activation for cleavage that is substantially higher than the energy of activation for cleavage of the above-described protecting groups. This difference in the relative amount of activation energy permits deprotection without releasing substantial amounts of the oligomeric molecule from the support. For example, contacting a peptide attached to a support via an MBHA linker with a weak acid (e.g., TFA) results in the preferential cleavage of protecting groups but does not result in substantial release of the deprotected peptide from the support because TFA is not a sufficiently strong nucleophile to cleave the MBHA first bond. To cleave the first bond and release the deprotected peptide, the coated-support must be contacted with a stronger acid (e.g., hydrofluoric acid (HF)). Additional examples of cleavage conditions to achieve the controlled release of deprotected peptides from a support are provided herein.

Referring to Table 1, substantially all of linkers #1–3 are cleavable at a first internal bond upon exposure to a strong acid, such as HF, TMSBr (trimethylsilylbromide), or TFMSA (trifluoromethanesulfonic acid). To achieve the controlled release of a deprotected peptide from a support to which the peptide is coupled via any of linkers #1–3, the peptide coated support is first deprotected and then exposed to a cleaving agent which is not as effective as a strong acid at cleaving the first bond. For example, a weak acid (e.g., TFA) is initially used to deprotect the peptide. Next, the deprotected peptide-coated support is exposed to a strong acid (e.g., HF) for a limited period of time to cleave a portion of the first bonds, thereby releasing a portion of the total peptide from the support. Other cleaving agents for cleaving a substantial number of the first bond of linkers #1–3 to achieve controlled release of the peptide include: TFA (a higher concentration or longer exposure time than is used to achieve deprotection); $CF_2ClCOOH$; $CFCl_2COOH$; $CCl_3COOH$; $CF_3CH_2COOH$; HCL; EM-radiation; and catalytic cleavage (i.e., exposure to a hydrogen donor catalyst, such a paladium).

Substantially all of linkers #4–5 are cleavable at a first internal bond upon exposure to a base, such as piperidine. These linkers are used in combination with tBoc chemistry for side chain and terminal amine protection to achieve the controlled release of deprotected peptides from the support. Specifically, a weak acid (e.g., TFA) is used to remove the protecting groups. Next, the deprotected peptide-coated support is exposed to a strong acid under limiting conditions (e.g., limited in time and/or concentration) to release some, but not all, of the peptides from the support. Other cleaving agents for cleaving the first bond of linkers #4–5 in a controlled manner include: weaker bases (i.e., bases weaker than piperidine); acids (as described above); EM-radiation; and catalytic cleavage.

Substantially all of linkers #6–8 are cleavable at a first internal bond upon exposure to light, e.g., ultraviolet (UV) light. These linkers are used in combination with either tBoc or Fmoc chemistry for side chain and terminal amine protection to achieve the controlled release of deprotected peptides. The controlled release of deprotected peptides is achieved by exposing the deprotected peptide coated support to any of the following cleaving reagents: EM-radiation, acids, bases and catalytic cleavage agents.

Substantially all of linkers #9–10 are cleavable at a first internal bond upon exposure to catalytic cleavage agents, e.g., hydrogen donors such as paladium. These linkers can be used in combination with either tBoc or Fmoc chemistry for side chain and N-terminal amine protection to achieve the controlled release of deprotected peptides. To deprotect the peptide, the coated support is exposed either to a weak acid (e.g., TFA) or to a strong acid (e.g., HF) for a limited period of time, depending upon whether Fmoc or tBoc chemistry, respectively, is used. The controlled release of deprotected peptides from the support is achieved by exposing the deprotected peptide coated support to any of the following cleaving reagents: EM-radiation, acids, bases and catalytic cleavage agents.

Linkers in addition to those listed in Table 1 and Table 2 are numerous as will be recognized by one of ordinary skill in the art, and may be selected based upon, for example, susceptibility to nucleophilic cleavage (described above) or electrophilic substitutions, availability, non-toxicity to the target in certain embodiments and usefulness with particular supports or beads. As discussed above, an important criterion for the selection of a first linker useful for the controlled release of peptide is the ability of the linker to be matched with a cleavage condition(s) that permits only partial release of the peptides. The selection of the cleaving agent may also be influenced by a variety of factors such as its ability to effectively cleave the oligomeric molecules from the linker in the desired environment of use and its non-toxicity to targets in the substrate (particularly when cleavage is carried out after the beads are applied to the substrate).

In some embodiments, cleavage is carried out prior to applying the beads to the substrate, whereby the oligomeric molecule simply remains associated with or coated upon the bead. It is believed that the oligomeric molecule is held in such association only by non-covalent forces such as electrostatic attraction. In other embodiments, cleavage is carried out after applying the beads to the substrate, whereby the oligomers are released into the substrate.

In certain embodiments a first substantial portion of multiple copies of a single oligomeric molecule is attached to a bead by a first linker and a second substantial portion of multiple copies of the single oligomeric molecule is attached to the same bead by a second linker. A substantial portion means enough to achieve the purposes of the invention. Since sequencing is desired, it is preferred that enough oligomeric molecules remain on the bead to permit sequencing after an amount of oligomeric molecules has been permitted to separate from the bead and initiate a detectable signal. Conversely, there should be enough molecules on each bead for release into the surrounding localized environment to permit initiation of a detectable signal upon interaction of the oligomeric molecule with a target. These amounts, of course, will vary with the selection of the particular assay and the conditions employed. In the preferred assay it is believed that less than 10 picomoles of peptide are necessary to obtain a detectable signal (possibly as low as 3 picomoles) and that approximately 10 picomoles are sufficient for sequencing.

In those embodiments in which peptides are linked to beads using two different linkers on each bead, one of the linkers can be cleavable in air saturated with trifluoroacetic acid (TFA), with the other being resistant to such treatment. Prior to application of the beads to the substrate, some of the peptides are released using the TFA "dry" method, i.e., by contacting the beads with the cleaving agent present in a gaseous state (described in greater detail below). The beads then are applied to the substrate. Peptides released as a result of cleavage by TFA of the covalent bond generally will diffuse away from the beads to initiate the signal. A bead in the vicinity of the signal can be collected (e.g., with forceps) and the peptide bound to the bead through the second linker can be sequenced or released using a second dry or "wet" condition for additional tests.

It will easily be understood by those of ordinary skill in the art that a single bead may even have two different oligomeric molecules attached to it by two or even four different linkers. Such embodiments are contemplated by the invention and the claims. When multiple linkers are employed to attach the oligomeric molecules to the beads, different advantages can be achieved. For example, the oligomeric molecules on a bead can be attached by three different linkers. Attachment via the first linker can be cleaved selectively in connection with a first assay to limit to, for example, a small fraction of the total number of possible molecules/beads (e.g., 1–10%) responsible for the signal. These beads then can be isolated. Attachment via the second linker can be cleaved selectively in connection with a second assay (in which the isolated beads are spaced at a greater distance from one another), to identify the isolated bead(s) responsible for the signal. Thereafter, the attachment via the third linker can be cleaved selectively, and the molecules on that isolated bead can be sequenced or otherwise subject to analysis.

As mentioned above, some assays according to the invention involve cleaving the covalent bond between the oligomeric molecule and the bead prior to applying the bead to the substrate. Surprisingly, it has been discovered that the molecules remain attached to their respective beads when the covalent bond is cleaved with the beads in a "dry" state. As illustrated in the Examples, beads can be placed in a test tube, dish or other container and then exposed to a gas such as air that is saturated with a cleaving agent (e.g., TFA). After sufficient time, the molecules are cleaved from their support beads but still adhere to the support beads, due to forces such as electrostatic attraction. Beads non-covalently coated with such molecules can be applied individually or sprinkled collectively onto a test apparatus for further analysis.

The various assays of the invention involve applying the beads with associated peptides to a substrate. The substrate can be any support that permits the beads to be substantially immobilized thereon and that causes oligomeric molecules associated with the beads to separate therefrom and diffuse therein. Preferably, the substrates are gels such as agarose or acrylamide. Thin layer chromatography plates also can be used in the assays of the invention. Generally, the substrate needs to provide a surface or volume on or in which controlled diffusion of the oligomeric molecule can occur.

The beads are applied to the substrate such that they are substantially spaced-apart. By substantially spaced-apart it is meant that the beads are sufficiently remote from one another whereby the peptides released from a particular bead generally do not mix with peptides released from neighboring beads. It should be understood, however, that it will be impractical to insure an ideal separation of beads particularly where huge libraries are employed, and that a detectable signal may result from diffusion of peptide from any number of adjacent beads in the vicinity of the signal. More than one bead then may need to be isolated and sequenced, and then retested. Thus, by spaced-apart, it is meant spaced enough apart to achieve the purposes of the invention.

The oligomeric molecules diffuse through the substrate and interact with a target. The target can be contained within a second substrate in contact with the first substrate. Thus, for example, the first and second substrates can be formed of the same material (e.g., polyacrylamide) but with the second substrate further including the target. The target can be any entity that is capable of interacting with a desired oligomeric molecule, and preferably is one that produces a visually detectable signal upon interaction with the desired oligomeric molecule. Such targets include the melanocytes that are the subject of U.S. patent application Ser. No. 07/732, 476, M. R. Lerner et al., filed Jul. 16, 1991 now U.S. Pat. No. 5,462,856 (PCT Publication WO92/01810, published Feb. 6, 1992), the entire disclosure of which is incorporated herein by reference. Generally, lower animal pigment cells are useful in that they change their degree of pigmentation quickly in response to stimulating agents such as light and melantonin. The particular melanophores of the foregoing patent application are continuous, long term cultures that have been engineered to contain the desired cell surface receptors, whereby binding to the receptor stimulates the pathway responsible for pigment aggregation/dispersion. Thus, peptide agonists of those receptors, for example, may be discovered using the protocols of this invention.

Pigment translocation assays employing the above-described melanophores, i.e., assays based upon the aggregation or dispersion of pigment, provide an attractive tool for screening a mobile peptide library (MPL). The stimulation of receptors resulting in activation of either adenyl cyclase or phospholipase C leads to pigment dispersion. Conversely, the stimulation of receptors which normally function to inhibit adenyl cyclase leads to pigment aggregation. Accordingly, the preparation of recombinant melanophores expressing exogenous G-protein coupled receptors permits the screening of complete MPLs for the presence of new agonists and antagonists. Such pigment translocation assays in combination with the instant invention provide a sensitive and versatile functional expression assay for evaluating the effects of ligand interactions with virtually any G-protein coupled receptor.

The applicants specifically do not intend to be limited to the particular detection signal or cell line that is employed, as a wide variety of such signals and cell lines are available. For example, COS cells (a well-known, monkey kidney cell-line) may be employed in detecting the ability of an oligomeric molecule to interact with a COS cell receptor involved in calcium channels. The change in calcium levels can be monitored by standard fluorescent assays well known to those of ordinary skill in the art. In addition, cultured tumor cells can be used for the detection of oligomeric molecules that potentially inhibit the growth of such cultured tumor cells. Further, nerve cells can be used for the detection of the ability of oligomeric molecules to stimulate growth of the nerve cells. As yet another example, cells genetically engineered to contain the beta-galactosidase coding sequence change color when a molecular entity turns on the regulatory elements controlling the beta-galactosidase coding sequence. Detecting a color change would indicate that a particular oligomeric molecule has affected the regulation of the beta-galactosidase coding sequence. Thus, pigment dispersion/aggregation, color changes, cell growth and cell death are merely examples of the particular systems useful in the assays of the invention.

Moreover, it is not necessary to employ a living cell as a component of the assay. For example, the assay may be a simple immunological binding assay, wherein the released oligomeric molecules are caused to diffuse into a gel and are brought into contact with a binding partner such as a monoclonal antibody coated on the bottom of the plate containing the gel or contained within a second substrate as described above. In this instance, the oligomeric molecules are labeled and detection is based upon observing the label attached to the antibody target (after appropriate washing steps). Other targets include antibody components (such as Fab fragments and recombinant antibodies containing the antigen-binding site) and cells that lyse upon interaction with the desired oligomeric molecules, e.g., due to the cytotoxic effect of the oligomeric molecule. Thus, it should be clear to those of ordinary skill in the art that the detection format is not meant to limit the invention.

The MPLs have been shown to be an invaluable tool for rapidly evaluating large numbers of peptides and their analogues (see e.g., Examples 2 and 3). In addition to identifying oligomeric molecules which interact with a target, the methods of the instant invention are useful for determining the relative potency of the oligomeric molecules for the target (see e.g., Example 2). Accordingly, the instant invention should prove to be useful for any assay in which the screening of large numbers of biological molecules (free from interference by competing biological molecules) is required, e.g., assays relating to identifying and cloning receptors, identifying ligands for receptors, drug design, structure/function studies and to designing molecular probes.

As described above, in certain preferred embodiments, the beads are separated from the target by a first substrate, e.g., a layer of substrate or the like that is free of target. This ensures that the signal results from interaction of the target (preferably contained within a second substrate) with 'native' oligomeric molecule that has diffused from the bead, and not from interaction of the target with the bead itself or with material attached to the bead such as a linker.

The invention may be better understood with reference to the following non-limiting examples.

EXAMPLES

Example 1

Synthesis of a Peptide Combinatorial Library including a Single Linker

A. Synthesis of an MPL:
(a) Materials:

Resin Beads: During this study, 1% DVB/polystyrene beads were used. However, other types of resins based on polystyrene with varying degree of cross linking with DVB (divinylbenzene) or polyamide could be used (Fields, G. B., et al., Principles and Practice of Solid-Phase Peptide Synthesis. In Synthetic Peptides: A User's Guide, G. A. Grant, ed., W. H. Freeman and Company, 1992, 77–183; Stewart, J. M., Young, J. D.; Solid Phase Peptide Synthesis, 2nd Ed., Pierce Chemical Co., Rockford, Ill., (1984); Atherton, E., Sheppard, R. C.; Solid Phase Peptide Synthesis: A practical approach, D. Rickwood and B. D. Hames, Eds. IRS Press, (1989)).

Linker/Handle: Peptide acids were synthesized on a 4-(hydroxymethyl)phenoxymethyl linker. Peptide amides were synthesized on a 4-(2', 4'-dimethoxyphenyl-Fmoc-aminomethyl)-phenoxy linker. These linkers, already attached to 1% DVB/polystyrene beads (100–200 mesh), were purchased from Nova Biochemicals (USA) or Peptide International (USA). The beads are also commercially available with the first amino acids attached to the linker.

Other types of linkers or handles which are capable of being cleaved under different conditions can be used to attach the peptides (or other oligomeric molecules) to the beads. The properties and synthesis of various linkers are described above and elsewhere (Fields, G. B., et al., (1992) supra.; Stewart, J. M., et al., (1984), supra.; Atherton, E., et al., 1989), supra.). Linker cleavage conditions include, for example, strong acids such as HF, mild acids such as 1%–100% TFA, bases such as piperidine, metal catalysts such as Pd and photo-excitation.

Amino Acids: Amino acids with temporary $N^{alpha}$-Fmoc protection are used. Permanent protection compatible with $N^{alpha}$-Fmoc protection is provided primarily by either ester and/or urethane derivatives based on tert-butanol. However amino acids with other types of $N^{alpha}$ protection such as tBoc and various types of side chain protections are optionally used for this purpose (Fields, G. B., et al., (1992), supra.; Stewart, J. M., et al., (1984), supra.; Atherton, E., et al., (1989), supra.). Synthesis and properties of Fmoc, tBoc and other amino acids and their active esters with varying side chain protections have been reviewed (Fields, G. B., et al., (1992), supra.; Stewart, J. M. et al., (1984), supra.; Atherton, E., et al., (1989), supra.).

The amino acid building blocks can be 20 genetically encoded L-residues, D-amino acids, synthetic amino acids, amino acids with side chain modifications such as sulfate groups, phosphate groups, carbohydrate moieties, etc.
(b) Methods:

Peptide Synthesis: Peptide synthesis can be performed using, for example, Fmoc chemistry (Fields, G. B., et al., (1992), supra.; Atherton, E., et al., (1989) supra.) or t-Boc chemistry (Fields, G. B., et al., (1992) supra.; Stewart, J. M., et al., (1984), supra.). The Fmoc strategy was utilized in this example.

Activation: During this study all amino acids were activated using 'In situ' reagents HBTU (Fields, C. G., et al., HBTU activation for automated Fmoc solid phase peptide synthesis: *Peptide Res.* 4 (1991) 95–101) and HOBt (Fields, G. B. and Noble, R. L., Solid phase peptide synthesis utilizing 9-Fluorenylmethoxycarbonyl amino acids: 35 (1990) 161–214) in DMF. Activation with active esters, preformed symmetrical anhydrides, acid halides or other types of 'in situ' reagents may also be used (Fields, G. B., et al., (1992), supra.; Stewart, J. M., et al., (1984), supra.; Atherton, E., et al., (1989), supra.).

Cleavage: During this study peptide cleavage from the beads was performed by exposing the beads to saturated TFA vapor.

Chemicals: Fmoc-Ala-OH, Fmoc-D-Ala-OH, Fmoc-Arg(Pmc)-OH, Fmoc-D-Arg(Pmc)-OH, Fmoc-Asn(Trt)-OH, Fmoc-D-Asn(Trt)-OH, Fmoc-Asp(OtBu)-OH, Fmoc-D-Asp(OtBu)-OH, Fmoc-Cys(Trt)-OH, Fmoc-Gln(Trt)-OH, Fmoc-D-Gln(Trt)-OH, Fmoc-Glu(OtBu)-OH, Fmoc-D-Glu-(OtBu)-OH, Fmoc-Gly-OH, Fmoc-His(Trt)-OH, Fmoc-D-His(Trt)-OH, Fmoc-Ile-OH, Fmoc-Leu-OH, Fmoc-D-Leu-OH, Fmoc-Lys(Boc)-OH, Fmoc-D-Lys(Boc)-OH, Fmoc-Met-OH, Fmoc-D-Met-OH, Fmoc-Phe-OH, Fmoc-D-Phe-OH, Fmoc-Pro-OH, Fmoc-D-Pro-OH, Fmoc-Ser(tBu)-OH, Fmoc-D-Ser(tBu)-OH, Fmoc-Sta-OH, Fmoc-Thr(tBu)-OH, Fmoc-D-Thr-(tBu)-OH, Fmoc-Trp(Boc)-OH, Fmoc-D-Trp-(Boc)-OH, Fmoc-Tyr(tBu)-OH, Fmoc-D-Tyr(tBu)-OH, Fmoc-Val-OH and Fmoc-D-Val-OH were purchased either from Peptide Internationals, Inc., Kentucky or Nova Biochemicals, California. DCM, DMF, NMP, piperidine, and TFA were supplied by Applied Biosystems, California. EtOH, MeOH, pyridine, KCN, ninhydrin and phenol were obtained from Aldrich Chemical Company, Inc., Wisconsin.

Procedure: 0.25 mmols of resin first was weighed. The weighed resin beads then was soaked in 10 ml NMP and transferred to an hour glass reaction vessel (Peptide International, Inc., Kentucky).

Deprotection: The resin was washed with 3×10 ml NMP and then was treated with 10 ml of 20% piperidine/NMP for 5 min. The piperidine/NMP was repeated with 10 ml of fresh 20% of piperidine/NMP for 20 min. The resin then was washed with 6×10 ml of NMP. The resin was resuspended in 10 ml of NMP and a 50 ml sample was removed for quantitative ninhydrin testing (Fields, G. B. and Noble, R. L.; Solid phase peptide synthesis utilizing 9-Fluorenylmethoxycarbonyl amino acids: 35 (1990) 161–214); If deprotection was ≧99%, the activation and coupling for next amino acid was carried out. If <99%, deprotection was repeated.

Activation and Coupling: 1.0 mmol of derivatized amino acid was dissolved in 2.5 ml of NMP. 2.0 ml of 0.45M HBTU +0.45 HOBt in DMF then was added. The amino acid/HBTU/HOBt solution was mixed for 10 min. and then transferred to the resin. 2.0 mmol (0.35 ml) of DIEA was added to the resin solution and allowed to react for 30 min. at room temperature while mixing. The resin was washed with 6×10 ml of NMP and was resuspended in 10 ml of NMP; A 50 ml sample was removed for quantitative ninhydrin testing; If coupling was ≧99%, deprotection of Fmoc group was initiated. If ≧99%, coupling was repeated.

End amino acid: the resin was treated with 10 ml of 20% piperidine/NMP for 5 min. The piperidine/NMP treatment was repeated with 10 ml of fresh 20% piperidine/NMP for 30 min. The resin then was washed with 6×10 ml of NMP and was resuspended in 10 ml of NMP. A 50 ml sample was removed for quantitative ninhydrin testing; If <99%, the deprotection was repeated. If ≧99%, the peptide resin then was washed with 4×20 ml of DCM followed by 4×20 ml of MeOH.

Cleavage: Peptide Cleavage was carried out using TFA vapor in order to keep the cleaved peptide in contact with its bead. The peptide resin (1–10 mg) was suspended in 1 ml of DCM and MeOH was added drop wise until beads start to sink. The suspension then was poured evenly onto a glass petri dish and allowed to air dry. The petri dish with beads was then placed in a desiccator already having in it a beaker containing 100% TFA to saturate the desiccator with TFA vapor. The reaction was allowed to proceed for 2–16 h at room temperature (20° C.–25° C.). After the TFA exposure, the dishes were sealed with parafilm and stored at −20° C.

Abbreviations:

DCM, dichloromethane;

DIEA, diisopropylethylamine;

DMF, N,N-Dimethylformamide;

DVB, divinylbenzene;

EtOH; ethanol;

Fmoc, 9-fluorenylmethyloxycarbonyl;

HBTU, [2-(1H-benzotriazol-1-yl)-1,1,3,3-tetramethyluronium]hexafluorophosphate;

HOBt, 1-hydroxybenzotriazole;

KCN, potassium cyanide;

MeOH, methanol;

NMP, N-methylpyrrolidone;

tBoc, tert-butyloxycarbonyl;

TFA, trifluoroacetic acid;

B. A Melanophore-Based Assay for Analysis of the Single Linker MPLs:

Melanophore cells (either transfected or non-transfected and as described in the above-identified patent application) were seeded (4×10$^6$) into 100 mm tissue culture plate (Falcon, N.J.). For transfected cells, the 100 mm tissue culture dishes were pre-coated with Cell-Tak (Collaborative Research, Inc., Massachusetts) at a concentration of 3.0 mg/cm$^2$. Media and conditions unless otherwise stated, were as described in the above-identified patent application. For wild type cells, no media changes are necessary and the cells can be used as soon as 24 hours after plating. For transfected cells, after the cells have attached to the surface (2–3 h), the media was removed and replaced with 20 ml of frog fibroblast conditioned media which is based on 70% L-15 media (Sigma) with 20% fetal bovine serum supplemented with L-Glutamine and Penicillin Streptomycin (Gibco). The cells were incubated at 27° C. for 12–72 h. Then 12–24 before the experiment, the media was removed and the cells were washed gently with 1×10 ml 70% EX-CELL 320 (JRH Biosciences, Kansas; 70% part A 29% water and 1% part B, hereinafter EX-CELL). Then cells were fed with 20 ml of fresh media (EX-CELL).

For receptors causing pigment dispersion 30 min. before the experiment, media was removed and replaced with a preparation containing Sea Plaque Agarose (FMC Bio Products, Michigan) EX-CELL media containing 2 nM melantonin. A 2.5% concentrated stock of Sea Plaque agarose in 0.7% PBS was autoclaved for 20 min. and then allowed to equilibrate in a 37° C. water bath. The 70% EX-CELL containing 2 nM melantonin was maintained at room temperature. The two were then mixed together to yield a solution that is 0.9% Sea Plaque agarose, 2 nM melantonin, in EX-CELL. This solution was then poured into the dish containing the cells and allowed to solidify at room temperature for a few minutes. The plate was then kept in the dark at room temperature with the lid off to prevent condensation, thereby allowing the agarose to gel and allowing the pigment to achieve an aggregated state (relatively light) due to the melantonin.

For receptors causing pigment aggregation, media was removed 30 min. before the experiment, and replaced with the Sea Plaque Agarose preparation. The plate was then exposed to low levels of light at room temperature, thereby allowing the agarose to gel and allowing the pigment to achieve a dispersed state (relatively dark) due to the room light (1.2 milliwatts white light per square centimeter).

After 30 min., approximately 100 single beads coated with peptide were sprinkled upon the agarose bed and video images (Videk, N.Y.) were captured at 0, 10, 20 and 30 min. time intervals. Images were taken with the culture plate placed on a glass plate raised approximately 4 inches above a light box that had been covered with red cellophane. Red cellophane was placed between the light source and the plate to prevent the light from stimulating the cells. Video images were subtracted to better view the response, although a response was detectable with the naked eye.

Positive beads or the agarose surrounding these beads were then removed from the plate and processed for sequence analysis. There was insufficient peptide remaining on the bead for sequencing, indicating that a second linker or a single linker cleavable under at least two different sets of cleavage conditions is necessary to ensure that an amount of peptide sufficient for amino acid sequencing remains on the bead.

Example 2

The Murine Bombesin Receptor: A Model for Demonstrating the utility of MPLs for studying ligand-receptor interactions The shortest peptide agonist at the bombesin receptor is bombesin (8–14) or Trp-Ala-Val-Gly-His-Leu-Met (Sequence ID. No. 1). To investigate the importance of the amino acid side chains at positions 1, 2 and 7 for peptide mediated receptor activation, a synthetic peptide combinatorial library based on the sequence was constructed in which the first two positions were filled by all possible combinations of 19 L-amino acids while four L-amino acids were incorporated at the seventh position. For the evaluation of the 1,444 peptides, the screening system disclosed herein was used. The results reveal that for agonist activity, the first two amino acids of the peptide must contain hydrophobic side chains and optimally, at least one of these should be aromatic. The bombesin peptide experiments described in this example can serve as a general model for the characterization of agonist peptides acting on G-protein coupled receptors.

Bombesin and related peptides such as gastrin-releasing peptide (GRP) actuate a wide range of biological processes including smooth muscle contraction, release of gastrointestinal hormones and enzyme secretion from the pancreas. In particular, bombesin is an autocrine growth factor for small-cell lung carcinoma cells which express high affinity bombesin receptors. The minimum number of amino acids required to elicit biological activity of the bombesin receptor encompasses bombesin residues 8–14. It has also been suggested that Trp21 (which is analogous to Trp8 in bombesin) plays an important role in binding of GRP to the bombesin receptor. Synthetic peptide combinatorial libraries offer an attractive new approach to generating large numbers of diverse peptides. Accordingly, we hypothesized that such libraries could facilitate structure-function studies between bombesin and its receptor to ultimately aid in the design of receptor antagonists.

The instant invention provides solutions to the two technical problems that needed to be addressed before a synthetic peptide combinatorial library (i.e., an SPCL) could be efficiently screened for agonists to the bombesin receptor. First, the instant invention provides a method for the controlled release of peptides from their support beads while simultaneously preventing intermixing with peptides derived from other beads in the collection. Second, the instant invention provides a simple functional bioassay for the bombesin receptor. Thus, the dual problems of controlled release and maintaining peptide order were solved by converting the SPCL into a mobile peptide library (MPL) by way of three developments: a trifluoroacetic acid (TFA) based gas phase procedure to release peptides from their solid supports, the use of a 4-methylbenzhydrylamine (MBHA) linker with slow release kinetics for gaseous TFA and the use of Fmoc chemistry to synthesize the peptides whose side chain protective moieties could be released by TFA.

For generation of the MPLs used in this study, Fmoc chemistry was used to synthesize peptides on a conventional t-Boc linker, MBHA, attached to polystyrene beads crosslinked with 1% divinylbenzene. The slow cleavage kinetics of the MBHA linker by TFA (gas) and the ability of TFA (gas) to remove the amino acid side chain protecting groups permitted the independent cleavage of the protecting groups while releasing a relatively small portion of the oligomeric molecules from the beads.

A. Cleavage Studies with litorin, a Bombesin receptor agonist, synthesized on an MBHA linker Synthetic litorin was synthesized on an MBHA-polystyrene resin (substitution level 0.95 mmoles/g) using Fmoc chemistry. All Fmoc-amino acids were coupled to the MBHA linker as follows: 1 mmol of derivatized amino acid was dissolved in 2.5 mL of N-methylpyrrolidone (NMP), 2.0 ml of 0.45M 2-[1H-benzotriazol-yl)-1,1,3,3-tetramethyl uronium hexafluorophosphate (HBTU) and 0.45M 1-hydroxybenzotriazole (HOBt) in N,N-dimethylformamide was added to the amino acid solution, the amino acid/HBTU/HOBt solution was mixed for 10 min. and then transferred to the resin. Next, 2.0 mmol of N,N-diisopropylethylamine was added to the resin solution and reacted for 30 min. at room temperature while mixing. The resin was deprotected by a 5 min. treatment followed by an additional 15 min. treatment with 20 % piperidine/NMP, filtered and rinsed six times with NMP. Two 2 mg of beads were removed for quantitative ninhydrin testing.

HPLC analysis was performed on a Pharmacia SMART System using a uRPC C2/C18 reverse phase column (2.1× 100 mm) utilizing a linear gradient of buffer A (0.1% TFA/water) to buffer B (0.085% TFA/acetonitrile). Peptide was eluted at a flow rate of 180 ml/min with a gradient of 10%–40% B over 20 minutes. Peptides were detected by measuring the absorbance at 214 nm. Cleavage analysis of beads for the kinetic study was performed according to the procedures described to produce MPLs (see part B, this Example); however, the litorin-bearing beads were exposed to gaseous TFA for time intervals of 0, 2, 4, 6 and 10 hours.

To demonstrate that gaseous TFA would cleave the amide bond anchoring the synthetic peptide with slow kinetics, litorin-bearing beads were sprinkled on a polyethylene sheet stretched between two teflon rings and exposed to gaseous TFA. Samples of beads were removed at specific time intervals and the amount of cleavage was quantified by HPLC analysis.

Figure 1B:
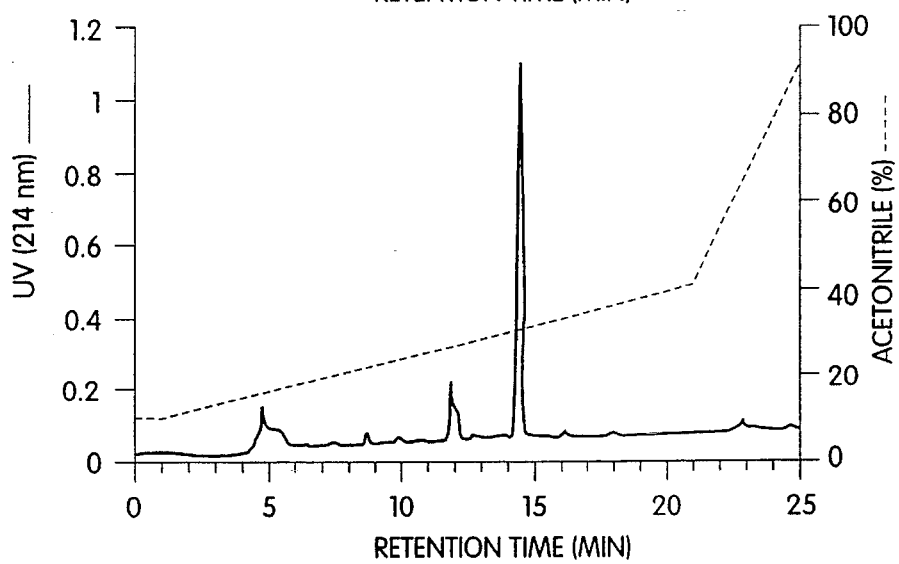
Figure 1C:
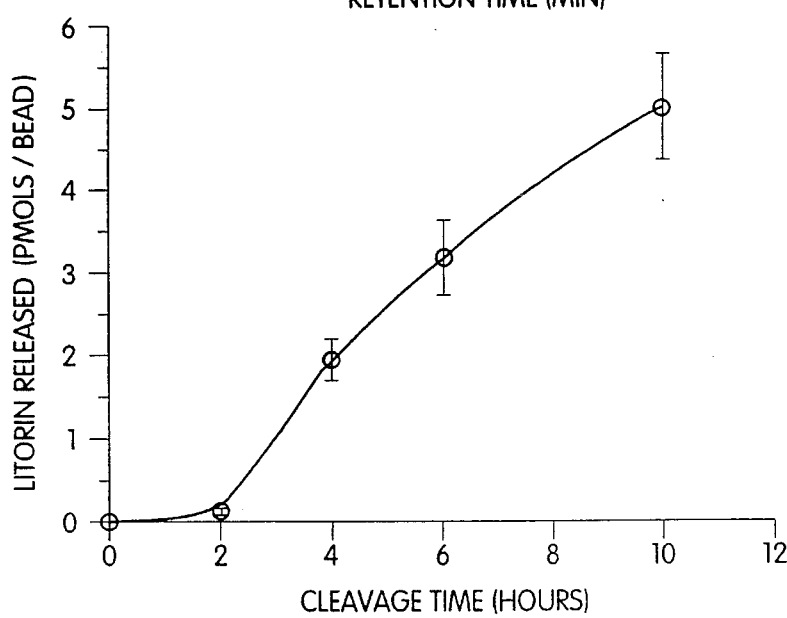

FIG. 1 illustrates HPLC analysis of synthetic litorin released from polystyrene beads using a gas phase cleavage procedure. FIG. 1-a shows HPLC fractionation of 500 pmol of litorin standard; FIG. 1-b shows HPLC fractionation of synthetic litorin cleaved from 225 beads by exposure to gaseous TFA for 6 hours; FIG. 1-c shows the kinetics of bond cleavage as determined by measuring the amount of litorin released from the beads upon exposure to gaseous TFA.

The results demonstrate that bond cleavage is a time dependent process in which less than or equal to approximately 5% of the peptide on the bead is cleaved from the bead after a 10 hour exposure to gaseous TFA. The slow induction period prior to initiation of cleavage appears to suggest the necessity of absorbing gaseous TFA to the bead to achieve a threshold concentration of cleaving agent prior to the agent cleaving the covalent bond. The biological activity of the free peptide released from (but still coated on) the bead was confirmed by applying the bead onto recombinant melanophores expressing murine bombesin receptor (Part C, this Example). In the melanophores, pigment dispersion can be effected via activation of adenyl cyclase or phospholipase C while pigment aggregation results from inhibition of adenyl cyclase. Since both states of intracellular pigment distribution are easily discernible with the naked eye, numerous recombinant GPCRs (G-protein coupled receptors) such as the bombesin receptor can be studies by monitoring ligand mediated melanosome translocation. (See, e.g., Graminski, G. R., et al., (1992) 268: 5957–5964).

The utility of the cleavage procedure, visa vis the release of biologically active agonists, was confirmed by repeating the above studies for many variants of synthetic analogues of a-MSH (Example 3), bombesin (this Example), thyrotropin releasing hormone ("TRH") and substance P receptor agonists (data not shown). In some instances, multiple rounds of cleavages were followed by assaying the released cleavage products for biological activity and sequencing the agonists remaining on the beads.

B. Construction of MPLs for Studying Bombesin Analogues.

Figures 2, 4:
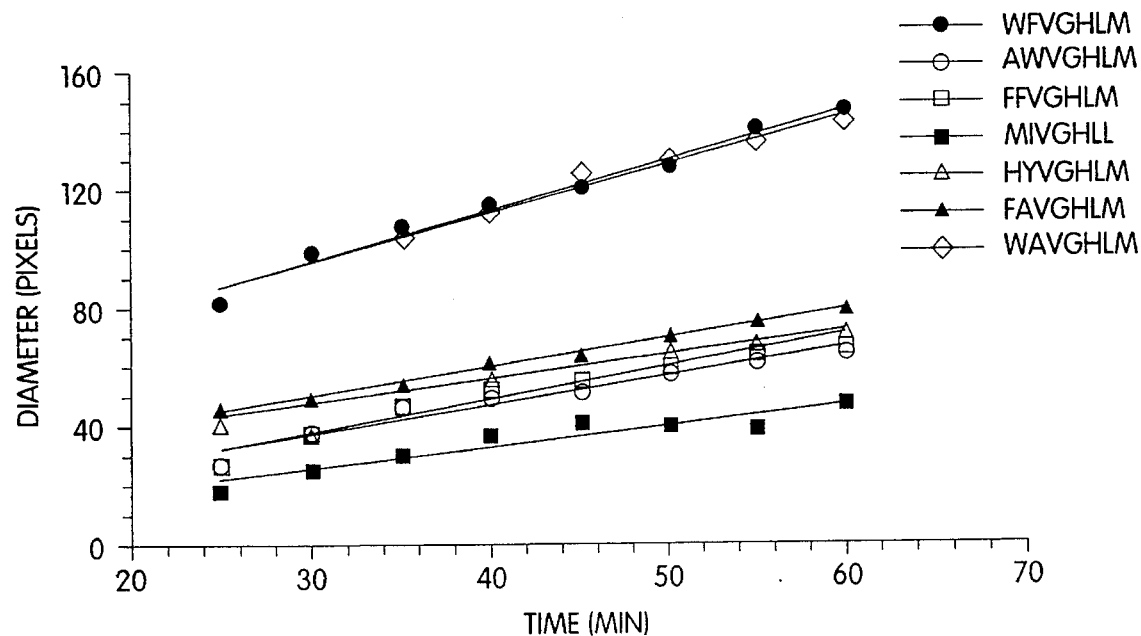
FIG. 2 illustrates the mobile protein libraries (MPLs) constructed for studying bombesin analogues; (Sequence I.D. No. 2)
FIG. 4 illustrates the dose response curves for the bombesin 7-mer agonists selected in FIG. 3.

The importance of Trp and Ala as the first two amino acids and of Met as the final amino acid of the bombesin analogue was investigated by constructing the MPL illustrated in FIG. 2. The first and second positions of the synthetic peptides were filled by all combinations of 19 L-amino acids and the seventh position was filled with by four L-amino acids to generate a library consisting of 1,444 distinct peptide sequences (see FIG. 2).

Each library was constructed on MBHA linkers using the Fmoc chemistry. Prior to preparation of the MPLs, side chain protection groups were removed in solution using cleaving reagent, washed, dried and cleaved for 6 hours by exposure to gaseous TFA. TFA absorbed to the beads was removed by drying under vacuum and residual amounts bound to the peptide or to the bead were neutralized by exposure to gaseous ammonia.

Specifically, the synthetic peptide combinatorial libraries for bombesin were prepared using methybenzhydrylamine (MBHA) polystyrene using (substitution level 0.95 mmols/g) and Fmoc chemistry (as described in part A; this Example) in combination with simultaneous multiple peptide synthesis using standard Fmoc protected L-amino acids.

For the preparation of MPLs, side chain protection groups attached to the amino acids were cleaved by stirring 10–100 mg of peptide bearing resin with 2 ml of 90% TFA/5% thioanisole/2.5 % ethanedithiol/2.5 % water (cleaving reagent) at room temperature for 1 hour. The cleavage reagent was filtered and the beads were thoroughly washed with dichloromethane (DCM), NMP and methanol and dried under vacuum for 6 hours. The peptide beads were then layered onto a thin film of polyethylene placed in a desiccator where they were kept under vacuum for 1 hour. Next, 10 ml of 100% TFA was transferred to the bottom of the deslocator, connected to the vacuum line (150–250 Hg mm) for 10 min. and then sealed. The reaction was allowed to proceed for 6 hours at room temperature (20–25 degrees C). Following exposure to TFA, the dish was transferred to a new dessiccator and dried under vacuum for 1 hour. Ten mls of 28% ammonium hydroxide solution were then transferred to the dessiccator, connected to the vacuum line for 10 min. and sealed. The neutralization reaction was allowed to proceed for 20 min. before drying the beads under vacuum for 1 hour.

C. Screening of the Bombesin 7-mer MPL using a dish plated with melanophore cells.

The bombesin MPL was screened for agonists using melanophore cells expressing the bombesin receptor. (FIG. 3). Melanophores were maintained in cell cultures as previously described (Potenza, M., and Lerner, M., Pigment Cell Res. 4:186–192 (1991); Potenza, M., and Lerner, M., Pigment Cell Res. 5:372–378 (1992)). Transient expression of bombesin receptor plasmid DNA (pJG3.6Br) in melanophores was achieved by electroporation (Graminski, G., et al., J. Biol. Chem. 268:5957–5964). To perform a ligand binding experiment, the media was removed from the 6 cm dish and replaced with 3.5 ml of 0.9% Sea Plaque Agarose prepared in fibroblast conditioned media containing 2 nM melantonin. The plate was then placed in the dark for 60 minutes, after which the MPL beads on a polyethylene film were applied to the agarose bed. Pigment dispersion induced by peptide analogues were monitored by video image subtraction (McClintock, T., et al., Anal. Biochem. 209:298–305 (1993)).

The illustrations shown in FIG. 3 depict 60 mm tissue culture dishes covered by confluent melanophores expressing the bombesin receptor and overlaid with agarose containing melantonin. The gel provided a matrix through which soluble peptides could easily diffuse. The melantonin activated the cells' melantonin receptor to induce pigment aggregation so that the plate acquired a light shade. Initial screening was performed by placing approximately 5000 beads from the MPL on top of the agarose.

Figure 3A:
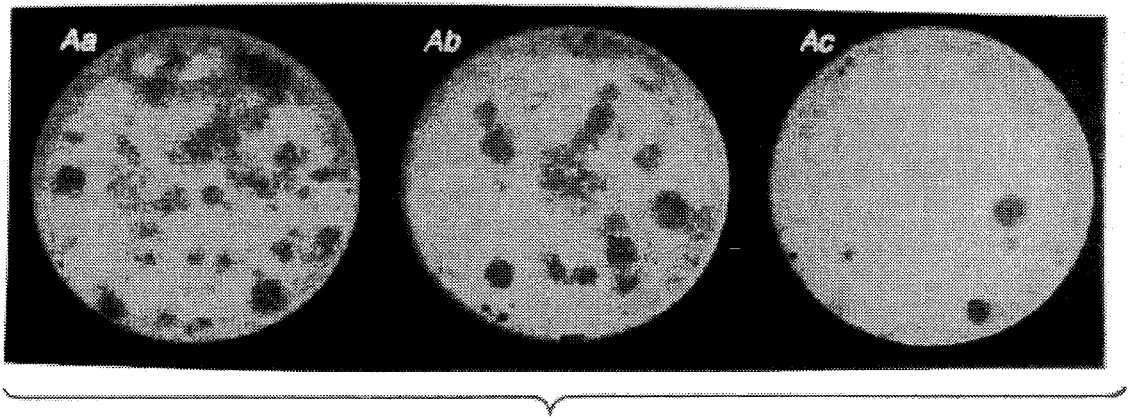
FIGS. 3A–3C illustrate the screening of a bombesin 7-mer (Sequence I.D. Nos. 5–11) MPL using a dish plated with melanophore cells.

As shown in FIG. 3, activation of the melanophores' endogenous melantonin receptor led to pigment aggregation within the cells (due to adenyl cyclase inhibition) so that the plate as a whole acquired a light shade. FIG. 3Aa shows a video image analysis resulting from 30 min. exposure to the MPL. Cells to which peptide agonists diffused, dispersed their melanosomes as evidenced by multiple and overlapping red circles (indicated by the dark circles in the present drawings). The dark circles represent a positive response from the bead, i.e., the bead contained a receptor agonist.

Figure 3B:
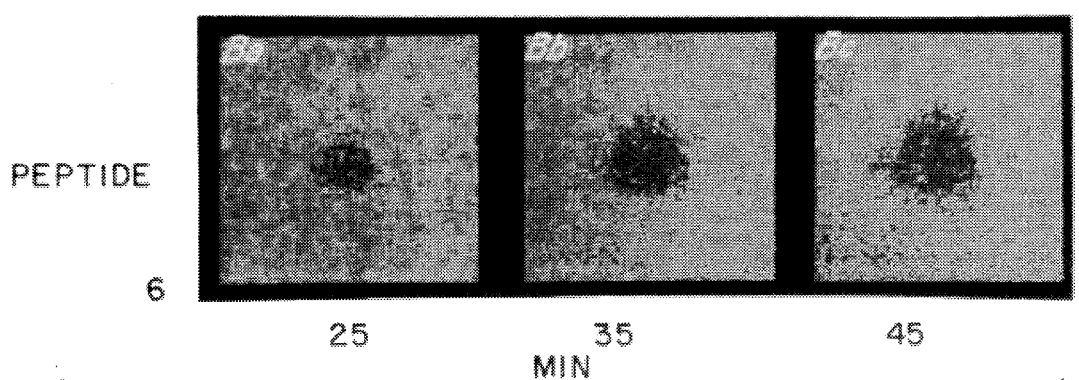
Figure 3C:
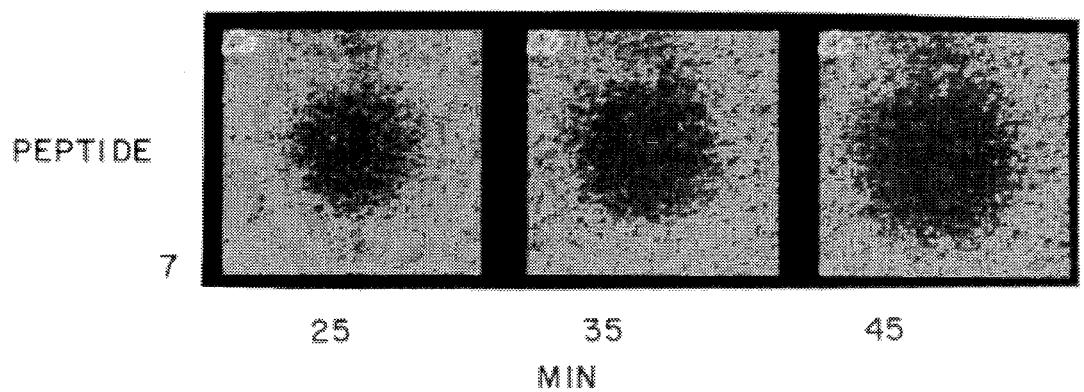

About 500 beads from a few selected postively-responding areas of the plate were then collected, washed, cleaved and reapplied for a second round of screening as shown in FIG. 3Ab. Finally, 52 beads were selected from four of the postive areas, reprepared and applied for a third round of screening. FIG. 3Ac reveals four circles of pigment darkening, each arising from a single bead at their centers. As peptides diffuse from their source beads, the circles of darkened pigment cells enlarged with time as seen in FIG. 3Ba–c and 3Ca–c for two selected positive beads. In particular, FIGS. 3B and 3C show the responses of recombinant melanophore cells to peptide from beads 6 (FAVGHLM) and 7 (WAVGHLM) at 25, 35 and 45 min, respectively.

After the final round of screening, more than about 90% of the peptide (approximately 200 pmols) remained attached to the bead. Each bead was washed and the peptide sequence contained on the bead was determined by placing the bead on a glass filter which was inserted into a peptide microsequencer (model 477A, Applied Biosystems) (see sequences listed in FIG. 4.) The sequencing studies established that the peptide present on any given single bead is sufficient for umambiguous sequence analysis as each bead sequenced contained between about 50–250 pmol of peptide (the lower limit of sensitivity of the instrument is in the range of 5 pmol). After sequencing the positively responding beads, the peptides contained thereon were synthesized in large quantities and their dose response curves were obtained as shown in FIG. 4.

D. Dose Response Curves of the Bombesin 7-mer Agonists.

Figure 5:
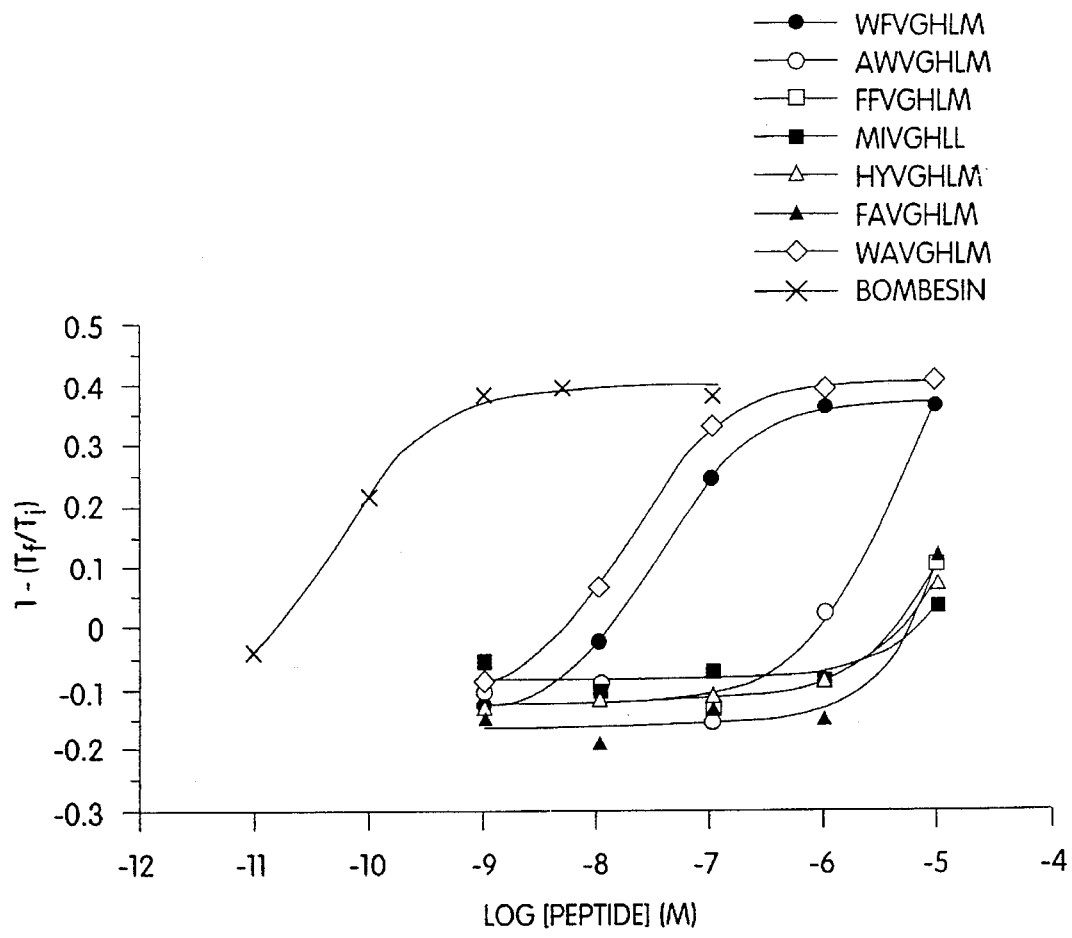
FIG. 5 illustrates the circle growth rates for positive-response beads.
Figure 6:
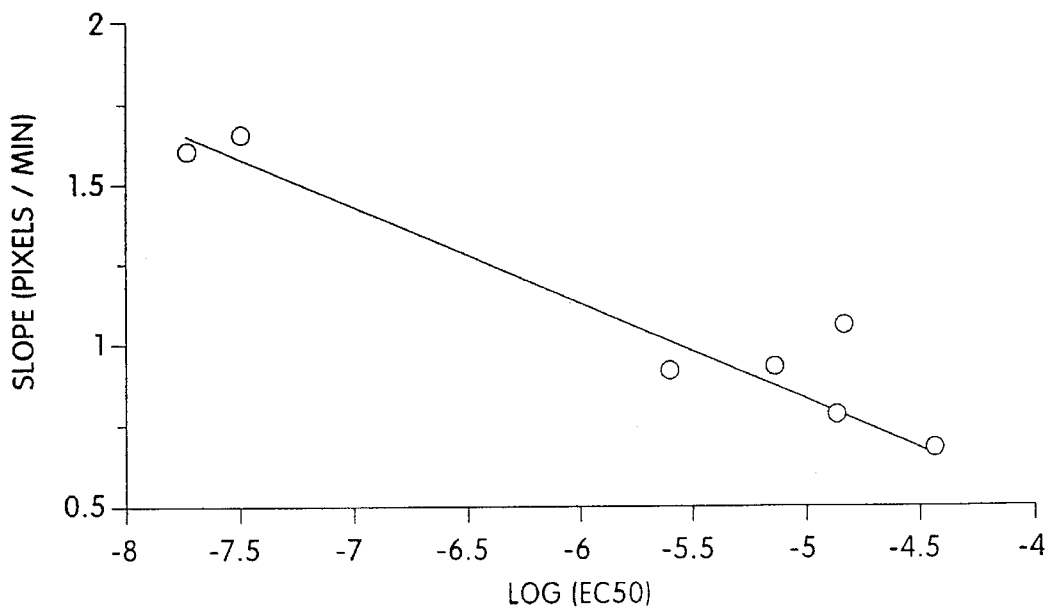
FIG. 6 illustrates the dependence of circle growth rate on EC50.

To confirm that the identified peptides were bombesin receptor agonists, they were resynthesized by standard means and dose response curves were obtained against melanophores expressing recombinant receptors as shown in FIG. 5. In particular, peptides were synthesized on Rink Amide MBHA resin (0.25 mmol scale) using Fmoc chemistry and were purified using HPLC and reverse phase chromatography on a C18 column. In FIG. 6, the abilities of the peptides to effect circle growth, expressed as the slopes of the lines in FIG. 5, are compared with their measured $EC_{50}$ values. The dose responses curves were obtained by microtiter plate assays using the melanophores cells transfected with pJG3.6BR plasmid DNA.

E. Measurement of Circle growth rates as indicative of $EC_{50}$ values.

The circle growth for positive beads (identified in this example, part D) at different time intervals was determined using the TCL-Image software (Biological Detection Systems, Pennsylvania) program with a MACIIfx computer. This determination was made to determine in what way $EC_{50}$ values affect the circle growth or rate of inducing pigment dispersion in melanophores. FIG. 5 shows the circle growth rate for each of the positive peptide beads calculated using the image analysis program. The relative circle diameter was plotted as a function of time and the results indicated that a linear fit could approximate at least the initial time points.

FIG. 6 shows the relationship between the slope of the circle growth rate and the $EC_{50}$ values calculated from FIG. 4. Although the exact mathematical relationship between $EC_{50}$ values and the rate of circle growth has not been established, these results reveal an approximately linear correlation which can be used to directly predict $EC_{50}$ values for future peptides without the need for their resynthesis and retesting. Besides rediscovering the initial peptide sequence, six new agonists were identified. In every case, the peptides have hydrophobic residues at both positions one and two. Further, with the exception of peptide MIVGHLL, at least one of the first two amino acids of each peptide contains an aromatic side chain group. Thus a high degree of unsaturation near the amino terminus of the ligands appears to play an important role in receptor activation. The fact that peptide MIVGHLL (Sequence ID. No. 2), which contains no aromatic side chain groups, is the least potent of the new agonists, but does have a Met at position 1, suggests that the lone pairs of electrons on the sulfur atom may partially compensate for a lack of an aromatic interaction important for receptor activation. In addition, every active peptide had Met at the 7th residue except for one instance of Leu. Thus, it appears that an indication of the relative potencies of a group of agonists (e.g., bombesin 7-met MPL) for a receptor, can be determined by measuring circle growth rates in the pigment translocation assay.

Example 3

Synthetic alpha-MSH: A Second Model for Demonstrating the utility of MPLs for studying ligand-receptor interactions A. Cleavage Studies with synthetic a-MSH, a G-protein coupled receptor agonist, synthesized on an MBHA linker:

(1). Synthesis of alpha-MSH and a control peptide:
9-fluorenylmethyloxycarbonyl (Fmoc) chemistry was used to synthesize alpha-MSH ("a-MSH") on Rink amide MBHA linkers attached to polystyrene beads containing 1% divinylbenzene and the fidelity of the construction was confirmed by fast atom bombardment mass spectrometry (data not shown).

Specifically, aMSH- and the negative control peptide-(Ser-Lys-Glu-Arg-His-Ser-Trp-Tyr-NH2(Sequence ID. No. 3)) containing beads were synthesized manually by Fmoc solid phase peptide synthesis (G. B. Fields and R. L. Noble, Int. J. Peptide Protein Res. 35, 161 (1990)) on Rink Amide MBHA resin (substitution level 0.46 mmols/g). The scale of the synthesis was 0.25 mmol and utilized protected L-amino acids.

Chemicals: Fmoc-Arg(Pmc)-OH, Fmoc-Glu(OtBu)-OH, Fmoc-Gly-OH, Fmoc-His(Trt)-OH, Fmoc-Lys(Boc)-OH, Fmoc-Met-OH, Fmoc-Phe-OH, Fmoc-Pro-OH, Fmoc-Ser(tBu)-OH, Fmoc-Trp(Boc)-OH, Fmoc-Tyr(tBu)-OH, Fmoc-Val-OH, and Rink amide MBHA resin were purchased from Nova Biochemicals, California. Dichloromethane (DCM), N,N-Dimethylformamide (DMF), N-methylpyrrolidone (NMP), piperidine, and TFA were supplied by Applied Biosystems, California. Ethanol, methanol (MeOH), pyridine, potassium cyanide, ninhydrin and phenol were obtained from Aldrich Chemical Company, Inc., Wisconsin. The resin was deprotected by a 3 min treatment, followed by an additional 15 min one with 10 mL 20% piperidine/NMP, filtered and rinsed six times with a total of 60 mL of NMP.

All Fmoc-amino acids were coupled with [2-(1H-benzotriazol-1-yl)-1,1,3,3-tetramethylurnium] hexafluorophosphate (HBTU) (C. G. Fields, et al., Peptide Res. 4, 95 (1991)) as follows: (a) 1 mmol of derivatized amino acid was dissolved in 2.5 mL of NMP; (b) 2.0 mL of 0.45M HBTU +0.45M 1-hydroxybenzotriazole (HOBt) in DMF was added to the amino acid solution; (c) the amino acid/HBTU/HOBt solution was mixed for 10 min and then transferred to the resin; (d) 2.0 mmol of diisopropylethylamine (DIEA) was added to the resin solution and reacted for 30 min at room temperature while mixing. The resin was filtered and rinsed six times with a total of 60 mL of NMP and 2.0 mg of the sample was removed for quantitative ninhydrin testing (V. K. Sarin, et al., Anal. Biochem. 117, 147 (1981)). Each Fmoc-amino acid was then deprotected as above. After the final deprotection the peptide was acetylated using 10 mL of acetylation mix containing 0.32M acetic anhydride/0.32M TEA in DMF.

(2) Characterization of a-MSH- and the congener peptide-containing beads:

2.0 mg of peptide-containing resin was cleaved by stirring in 100mL of 90% TFA 5% thioanisole/2.5% ethanedithiol/2.5% water at room temperature for 1 h. The cleavage mixture was filtered, diluted to 3.0 mL with water, extracted three times with equal volumes of diethyl ether and then freeze dried. The crude peptide was purified using HPLC and characterized by both fast atom bombardment mass spectrometry (FAB-MS) and analytical HPLC. The a-MSH standard used for comparison was a gift from Dr. Aaron Lerner. Analytical and Preparative HPLC was performed on Pharmacia SMART System using mRPC C2/C18 reverse phase column (2.1×100 mm). Peptide was eluted at a flow rate of 180 ml/min with a gradient of 10%–40% B over 20 min, where buffer A is 0.01% TFA/water and buffer B is 0.085% TFA/acetonitrile. Peptides were detected at 214 nm. FAB-MS was performed on a VG ZAB-SE mass spectrometer in the Comprehensive Cancer Center at Yale University School of Medicine.

(3) Peptide Cleavage from beads by TFA vapor:

To demonstrate that gaseous TFA is capable of severing the amide bond anchoring the synthetic peptide, beads were sprinkled onto a glass plate and exposed to acid vapors for 10 hours as described herein. The peptide resin (1–10 mg) was suspended in 1 mL of DCM:MeOH (1:1) and poured evenly onto a glass petri dish. After the DCM/MeOH evaporated, the dish was placed in a desiccator and dried further under vacuum for 1 h. Next, 10 mL of 100% TFA in a beaker was transferred to the desiccator which was reconnected to the vacuum line for 30 min and then sealed. The reaction was allowed to proceed for 10 h at room temperature (20° C.–25° C.). Following exposure to TFA, the dish was removed from the desiccator and sealed with parafilm.

Figure 7A:
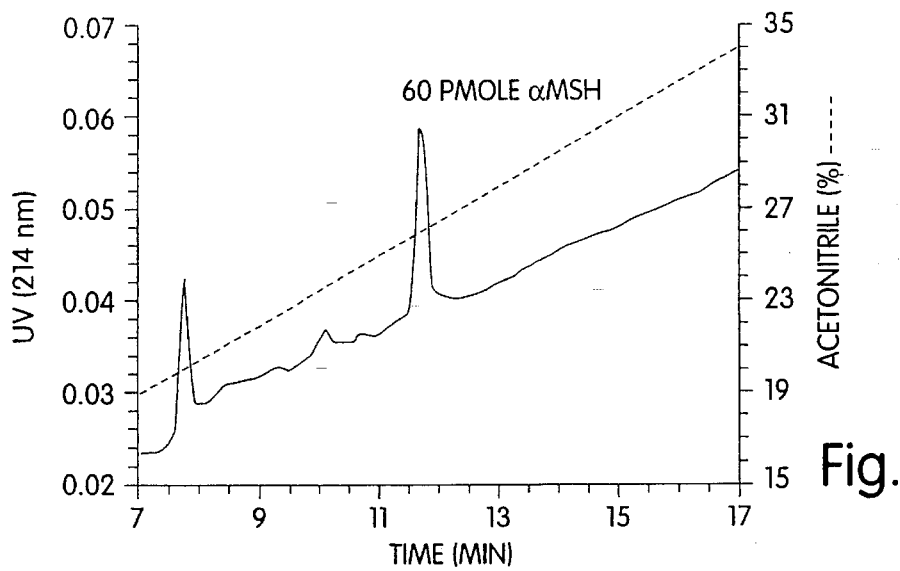
Figure 7B:
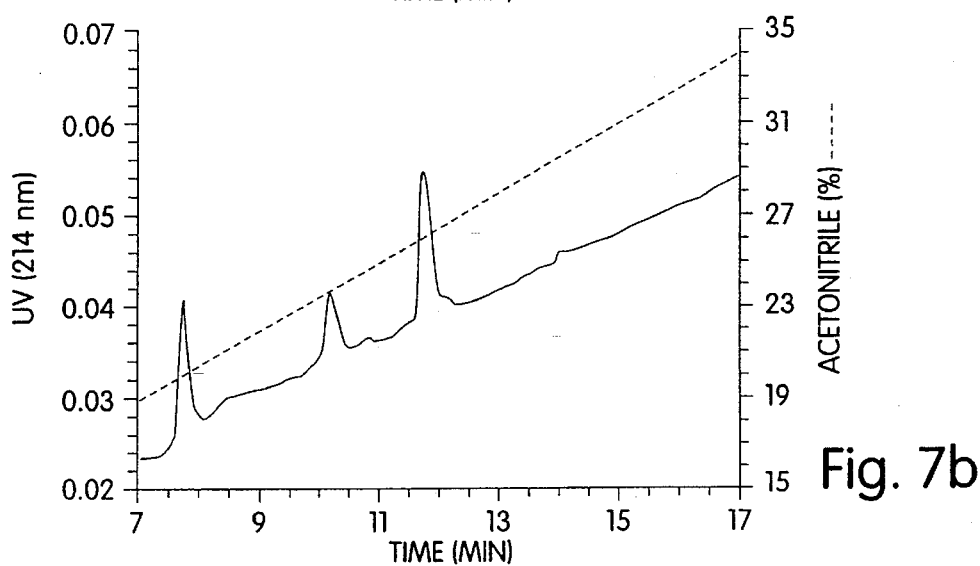
Figure 7C:
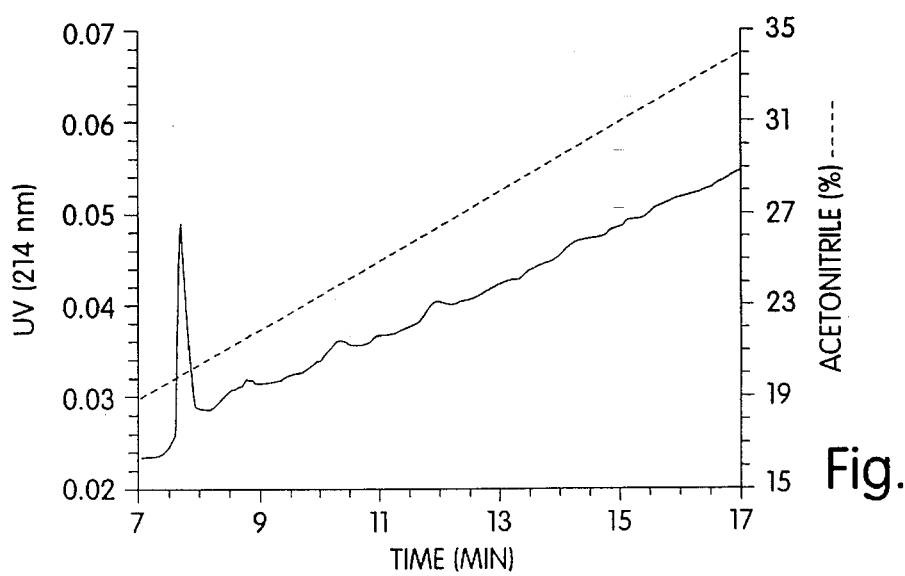

The fractionation of 60 pmole of an a-MSH standard by analytical HPLC is depicted in FIG. 7a. FIG. 7b shows that synthetic hormone cleaved from beads, by exposure to TFA gas, migrates identically to the control. This confirms not only that the bonds linking the peptides to the beads have been successfully broken, but that the covalent links between protecting groups used in the synthesis of the peptides, and the peptides' amino acid side chains, have also been severed. FIG. 7c illustrates that the dry release method frees essentially all peptide from their beads as there is little detectable a-MSH remaining if the gas phase treated resin is washed, and then reexposed to TFA for a second time but in solution.

The results indicate that, in principle, an entire SPCL could be rapidly converted into a MPL by exposing it to TFA vapor. The efficacy of such a procedure was demonstrated with the creation of a micro MPL based on the sequence of bombesin as previously described (Example 2).

B. Screening of a-MSH- and its congener peptide-beads with melanophore cells.

a-MSH and its congener peptide (cp) were screened using a culture dish plated with melanophore cells. Melanophores were maintained in cell culture as previously described (A. Daniolos, et al., Pigment Cell Res. 3, 38 (1990); M. N. Potenza, M. R. Lerner, Pigment Cell Res. 4, 186 (1991)). Four million cells were seeded into a 100 mm tissue culture plate (actual internal diameter was 85 mm) in 20 mL of frog fibroblast conditioned media and incubated at 27° C. for 72 h. For an experiment, the media was removed from the dish and replaced with 9 mL of 0.9% Sea Plaque Agarose (FMC Corporation) prepared in fibroblast conditioned media containing 20 nM melantonin. The plate was then placed in the dark for thirty min, after which beads coated with a-MSH or the cp, were sprinkled on the agarose bed and the pigment dispersion response was monitored by photography.

Figure 8A:
FIGS. 8A–8C illustrate the results of the pigment dispersion assay for measuring the bioactivity of a-MSH peptides selected in FIG. 7. The illustration of photograph displayed in FIG. 8a is a 100 mm tissue culture dish covered by confluent melanophores that had been overlaid for thirty minutes with a 1.6 mm thick agarose gel containing 20 nM melantonin.
Figure 8B:
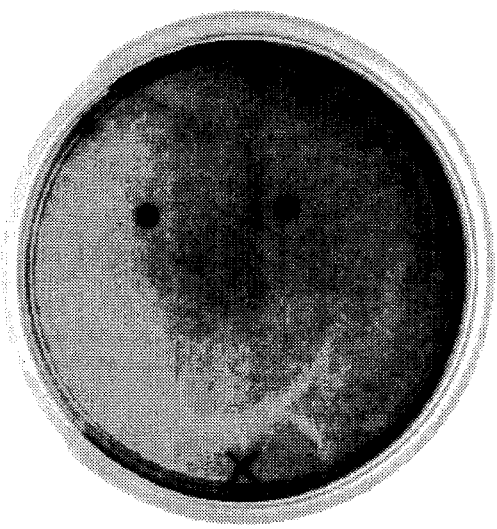
Figure 8C:
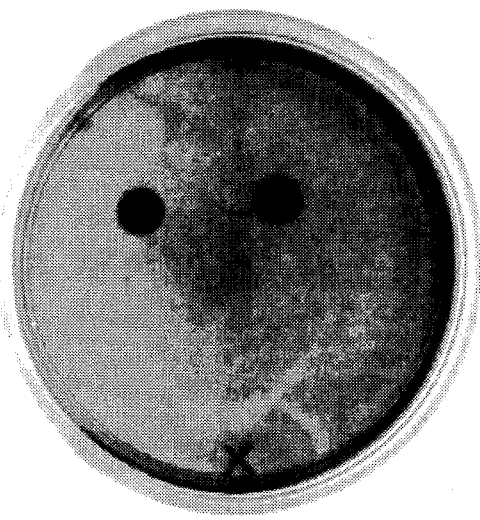

The free peptide released from, but still coated onto the beads, was biologically active as indicated in the melanocyte pigment translocation assay (see FIG. 8). The illustration of a photograph displayed in FIG. 8a is of a 100 mm tissue culture dish covered by confluent melanophores that had been overlaid for thirty minutes with a 1.6 mm thick agarose gel containing 20 nM melantonin. The gel served both to protect the pigment cells and to provide a medium through which soluble peptide could easily diffuse. Activation of the cells' endogenous melantonin receptors led to an inhibition of adenyl cyclase and pigment aggregation within the cells so that the plate as a whole took on a light shade. Ten minutes after two a-MSH-bearing, and two control peptide-bearing, TFA-treated beads were placed on the surface of the gel, (see FIG. 8b). Cells to which a-MSH had diffused, dispersed their melanosomes as evidenced by the two dark circles seen in the top half of the plate. The beads coated with cp were placed at similar positions in the lower half of the dish but their locations are not readily discernable. Because the synthesis of the cp utilized the same 5 amino acid side chain protecting groups involved in the creation of a-MSH, the lack of a pigment dispersion response shows that none of these masking molecules interfered with the assay by stimulating the pigment cells themselves. As peptides continued to diffuse outward from the four source beads, the circles of responding pigment cells surrounding the two a-MSH bearing beads enlarged as seen in FIG. 8c (30 minutes after placement of the beads).

EQUIVALENTS

Those skilled in the art will be able to ascertain, using no more than routine experimentation, many equivalents of the specific embodiments of the invention described herein. These and all other equivalents are intended to be encompassed by the following claims.

---

We claim:

1. A method for detecting the interaction between a peptide and a target, comprising:

(I) placing the target in a container;

(ii) overlaying the target with a substrate that is free of the target, the substrate constructed and arranged to permit only substantially localized diffusion of the peptides therein;

(iii) applying a plurality of beads to the surface of the substrate in a manner such that the beads are separated from the target by the substrate and such that the beads are substantially spaced-apart from one another and are immobilized on the substrate, each bead having associated therewith multiple copies of only a single peptide, wherein at least a substantial portion of the multiple copies is associated with each bead via non-covalent bonds;

(iv) allowing the substantial portion of the multiple copies to diffuse through the substrate and interact with the target, thereby resulting in a localized signal at the target;

(v) detecting the localized signal; and (vi) associating the localized signal with one or a limited number of the plurality of beads applied to the substrate.

2. The method of claim 1, further comprising (vii) isolating a bead in the vicinity of the localized signal; and (viii) sequencing the peptide associated with the bead in the vicinity of the localized signal.

3. The method of claim 1, wherein the target is a living cell.

4. A method for detecting the interaction between a peptide and a target comprising:

(I) attaching linkers to a plurality of beads;

(ii) attaching a plurality of peptides to the beads via covalent bonds to the linkers, each bead having associated therewith multiple copies of only a single peptide;

(iii) cleaving at least some of the covalent bonds so that at least a substantial portion of the multiple copies are associated with each bead via noncovalent bonds;

(iv) placing the target in a container;

(v) overlaying the target with a substrate that is free of the target, the substrate constructed and arranged to permit only localized diffusion of the peptides therein;

(vi) applying the plurality of beads to the substrate in a manner such that the beads are separated from the target by the substrate and such that the beads are substantially spaced-apart from one another and are immobilized on the substrate;

(vii) allowing the substantial portion of the multiple copies to diffuse through the substrate and interact with the target, thereby resulting in a localized signal at the target;

(vii) detecting the localized signal;

(ix) associating the localized signal with one or a limited number of the plurality of beads applied to the substrate;

(x) isolating a bead in the vicinity of the localized signal;

(xi) sequencing the peptide at the bead in the vicinity of the localized signal.

5. A method for determining the relative potency of an interaction between a peptide and a target, the method comprising:

(I) placing the target in a container;

(ii) overlaying the target with a substrate that is free of the target, the substrate constructed and arranged to permit only localized diffusion of the peptides therein;

(iii) applying a plurality of beads to the substrate in a manner such that the beads are separated from the target by the substrate and such that the beads are substantially spaced-apart from one another and are immobilized on the substrate, each bead having associated therewith copies of only a single peptide, wherein at least a substantial portion of the multiple copies is associated with each bead via non-covalent bonds;

(iv) allowing the substantial portion of the multiple copies to diffuse through the substrate and interact with the target, thereby resulting in a localized signal associated with the target;

(v) associating the localized signal with one or a limited number of the plurality of beads applied to the substrate;

(vi) measuring the localized signal at pre-selected time intervals; and (vii) determining the rate of change of the localized signal as a function of the time intervals, whereby the rate of change is proportional to the potency of the interaction between the peptide and the target.

* * * * *

UNITED STATES PATENT AND TRADEMARK OFFICE
CERTIFICATE OF CORRECTION

PATENT NO. : 5,601,992
DATED : 2/11/97
INVENTOR(S) : Michael Lerner, Ethan Lerner, Channa Jayawickreme It is certified that error appears in the above-identified patent and that said Letters Patent is hereby corrected as shown below:

Column 1, line 11, insert the following:

The invention identified above is a subject invention under 35 U.S.C. 200, et seq., and the Standard Patent Rights Clause at 37 C.F.R. 401.14 or F.A.R. 52.227-11, which are included among the terms of the grant/contract award from the Public Health Service/National Institutes of Health.

Signed and Sealed this

First Day of June, 1999

Attest:

Attesting Officer

Q. TODD DICKINSON

Acting Commissioner of Patents and Trademarks